(12) United States Patent
Fenge et al.

(10) Patent No.: US 8,697,440 B2
(45) Date of Patent: Apr. 15, 2014

(54) COMPOSITIONS AND METHODS FOR PRODUCING GAMMA-CARBOXYLATED PROTEINS

(75) Inventors: Christel Fenge, Södertälje (SE); Ann Lövgren, Mölndal (SE); Anders Thelin, Mölndal (SE)

(73) Assignee: Medimmune Limited, Cambridge (GB)

( * ) Notice: Subject to any disclaimer, the term of this patent is extended or adjusted under 35 U.S.C. 154(b) by 714 days.

(21) Appl. No.: 12/950,713

(22) Filed: Nov. 19, 2010

(65) Prior Publication Data

US 2011/0092429 A1 Apr. 21, 2011

Related U.S. Application Data

(63) Continuation of application No. 10/964,888, filed on Oct. 14, 2004, now Pat. No. 7,842,477.

(30) Foreign Application Priority Data

Oct. 14, 2003 (GB) .................................. 0324044.7

(51) Int. Cl.
C12N 5/07 (2010.01)
C12N 15/00 (2006.01)

(52) U.S. Cl.
USPC ..... 435/358; 435/348; 435/254.2; 435/320.1; 435/193; 536/24.1

(58) Field of Classification Search
None
See application file for complete search history.

(56) References Cited

U.S. PATENT DOCUMENTS

| | | | |
|---|---|---|---|
| 4,404,187 A | 9/1983 | Schwinn et al. | |
| 4,599,308 A | 7/1986 | Hamer et al. | |
| 4,784,950 A | 11/1988 | Hagen et al. | |
| 5,118,614 A | 6/1992 | Rybák et al. | |
| 5,122,458 A | 6/1992 | Post et al. | |
| 5,648,254 A | 7/1997 | Mulvihill et al. | |
| 5,866,122 A | 2/1999 | Turecek et al. | |
| 5,958,893 A | 9/1999 | Welsh et al. | |
| 5,965,789 A | 10/1999 | Lubon et al. | |
| 6,039,945 A | 3/2000 | Turecek et al. | |
| 6,165,974 A | 12/2000 | Turecek et al. | |
| 6,224,862 B1 | 5/2001 | Turecek et al. | |
| 6,224,864 B1 | 5/2001 | Argoudelis et al. | |
| 6,342,372 B1 | 1/2002 | Dubensky et al. | |
| 6,413,737 B1 | 7/2002 | Olsen et al. | |
| 7,482,141 B2 | 1/2009 | Stafford et al. | |
| 7,842,477 B2 * | 11/2010 | Fenge et al. | 435/69.1 |
| 7,989,193 B2 | 8/2011 | Lövgren | |
| 8,206,967 B2 | 6/2012 | Harrysson et al. | |
| 2002/0106381 A1 | 8/2002 | High | |
| 2004/0197858 A1 | 10/2004 | Yonemura et al. | |
| 2005/0164367 A1 | 7/2005 | Fenge et al. | |
| 2008/0045453 A1 | 2/2008 | Drohan et al. | |
| 2008/0312127 A1 | 12/2008 | Lovgren | |
| 2009/0047273 A1 | 2/2009 | Harrysson et al. | |
| 2011/0092429 A1 | 4/2011 | Fenge et al. | |

FOREIGN PATENT DOCUMENTS

| | | |
|---|---|---|
| EP | 0052827 | 6/1982 |
| EP | 0607392 | 7/1994 |
| EP | 0700682 | 3/1996 |
| EP | 1405910 | 4/2004 |
| EP | 1405912 | 4/2004 |
| EP | 1407780 | 4/2004 |
| EP | 1676911 | 7/2006 |
| WO | WO88/03926 | 6/1988 |
| WO | WO89/12685 | 12/1989 |
| WO | WO92/01795 | 2/1992 |
| WO | WO92/19636 | 11/1992 |
| WO | WO96/34966 | 11/1996 |
| WO | WO99/33983 | 7/1999 |
| WO | WO01/04146 | 1/2001 |
| WO | WO01/07068 | 2/2001 |
| WO | WO02/29045 | 4/2002 |
| WO | WO02/29083 | 4/2002 |
| WO | WO2005/030039 | 4/2005 |
| WO | WO2005/038019 | 4/2005 |
| WO | WO2005/040367 | 5/2005 |
| WO | WO2006/067116 | 6/2006 |
| WO | WO2006/110083 | 10/2006 |
| WO | WO2007/065173 | 6/2007 |

OTHER PUBLICATIONS

Bajaj et al. "Isolation and Characterization of Human Factor VII. Activation of Factor VII by Factor X" J. Biotechnol. 1981 (256) 253-259.
Bajaj et al. "A Simplified Procedure for Purification of Human Prothrombin, Factor IX and Factor X" Prep. Biochem. 1981 (11) 397-412.
Bandyopadhyay et al. "γ-Glutamyl carboxylation: an extracellular posttranslational modification that antedates the divergence of molluscs, anthropods, and chordates" Proc. Natl. Acad. Sci. 2002 (99) 1264-1269.
Begley et al. "A conserved motif within the vitamin K-dependent carboxylase gene is widely distributed across animal phyla" J. Biol. Chem. 2000 (275) 36245-36249.
Bentley et al. "Differential Efficiency of Expression of Humanized Antibodies in Transient Transfected Mammalian Cells" Hybridoma. 1998 (17) 559-567.
Bishop et al. "Comparison of Recombinant Human Thrombin and Plasma-Derived Human α-Thrombin" Sem Throm Hem. 2006 (32) 86-97.
Broun et al. "Catalytic Plasticity of Fatty Acid Modification Enzymes Underlying Chemical Diversity of Plant Lipids" Science. 1998 (282) 1315-1317.

(Continued)

Primary Examiner — Jim Ketter

(57) ABSTRACT

The present invention relates to methods and tools for producing large quantities of gamma-carboxylated protein comprising: (i) culturing a cell adapted to express a protein which requires gamma-carboxylation and γ-glutamyl carboxylase in a ratio of at least 10:1, under conditions suitable for expression of both proteins, and (ii) isolating gamma-carboxylated protein.

22 Claims, 3 Drawing Sheets

(56) References Cited

OTHER PUBLICATIONS

Camire et al. "Enhanced γ-Carboxylation of Recombinant Factor X Using a Chimeric Construct Containing the Prothrombin Propeptide" Biochemistry. 2000 (39) 14322-14329.
Clark et al. "The Secreted Protein Discovery Initiative (SPDI), a Large-Scale Effort to Identify Novel Human Secreted and Transmembrane Proteins: A Bioinformatics Assessment" Genome Res. 2003 (13) 2265-2270.
Cote et al. "Characterization of a stable form of human meizothrombin derived from recombinant prothrombin (R155A, R271A, and R284A)," J. Biol. Chem. 1994 (269) 11374-11380.
Czerwiec et al. "Expression and characterization of recombinant vitamin K-dependent γ-glutamyl carboxylase from an invertebrate, *Conus textile*" Eur. J. Biochem. 2002 (269) 6162-6172.
Fair et al. "Biosynthesis and Secretion of Factor VII, Protein C, Protein S, and the Protein C Inhibitor From a Human Hepatoma Cell Line" Blood. 1986 (67) 64-70.
Falkner et al. "High Level Expression of Active Human Prothrombin in a Vaccine Virus Expression System" Thrombosis and Haemostasis. 1992 (68) 119-124.
Fischer et al. "Purification of recombinant human coagulation factors II and IX and protein S expressed in recombinant Vaccinia virus-infected Vero cells" Journal of Biotechnology. 1995 (38) 129-136.
Gamma Glutamyl Carboxylase. UniPro Database. [online], [retrieved on Jan. 1-14, 2010] Retrieved from the UniPro Database using Internet <URL: http://www.uniprot.org/uniprot/?query=gamma+glutamyl+carboxylase&sort=score>.
Gustafsson et al. "Codon bias and heterologous protein expression" Trends in Biotechnol. 2004 22(7) 346-353.
Hallgren et al. "Carboxylase overexpression effects full carboxylation but poor release and secretion of a factor IX: implications for the release of vitamin K-dependent proteins" Biochemistry. 2002 (41) 15045-15055.
Harvey et al. "Mutagenesis of the γ-carboxyglutamic acid domain of human factor VII to generate maximum enhancement of the membrane contact site" J. Biol. Chem. 2003 (278) 8363-8369.
Hellstern et al. Preface Thrombosis Research. 1999 (95) S1.
Hellstern et al. "Prothrombin Complex Concentrates: Indications, Contraindications, and Risks: A Task Force Summary" Thrombosis Research. 1999 (95) S3-S6.
Hellstern "Production and Composition of Prothrombin Complex Concentrates: Correlation between Composition and Therapeutic Efficiency" Thrombosis Research. 1999 (95) S7-S12.
Herlitschka et al. "Overexpression of human prothrombin in permanent cell lines using a dominant selection/amplification fusion marker" Protein Expression and Purification. 1996 (8) 358-364.
Himmelspach et al. "A Fully Recombinant Partial Prothrombin Complex Effectively Bypasses fVII in Vitro and in Vivo" Thromb Haemost. 2002 (88) 1003-1011.
Jorgensen et al. "Expression of completely γ-carboxylated recombinant human prothrombin" J. Biol. Chem. 1987 (262) 6729-6734.
Kaufman et al. "Expression, Purification, and Characterization of Recombinant γ-Carboxylated Factor IX Synthesized in Chinese Hamster Ovary Cells" J. Biol. Chem. 1986 (261) 9622-9628.
Kini et al. "The intriguing world of prothrombin activators from snake venom" Toxicon. 2005 (45) 1133-1145.
Köhler "Thrombogenicity of Prothrombin Complex Concentrates" Thrombosis Research. 1999 (95) S13-S17.
Koresawa et al. "Synthesis of a New Cre Recombinase Gene Based on Optimal Codon Usage for Mammalian Systems" J. Biochem. 2000 (127) 367-372.
Kozak "Point Mutations Define a Sequence Flanking the AUG Initiator Codon That Modulates Translation by Eukaryotic Ribosomes" Cell. 1986 (44) 283-292.
Kozak "Downstream Secondary Structure Facilitates Recognition of Intiator Codons by Eukaryotic Ribosomes" Proceedings of the National Academy of Sciences of the United States of America. 1990 (87) 8301-8305.
Kozak "An analysis of 5'-noncoding sequences from 699 vertebrate messenger RNAs" Nucleic Acids Research. 1987 (15) 8125-8148.

Li et al. "Identification of the gene for vitamin K epoxide reductase" Nature. 2004 (427) 541-544.
Lingenfelter et al. "Isolation of the Human γ-Carboxylase and a γ-Carboxylase-Associated Protein from Factor IX-Expressing Mammalian Cells" Biochemistry. 1996 (35) 8234-8243.
Lucas et al. "High-level production of recombinant proteins in CHO cells using a dicistronic DHFR intron expression vector" Nucleic Acids Research. 1996 (24) 1774-1779.
Malhotra et al. "The kinetics of activation of normal and γ-carboxyglutamic acid-deficient prothrombins," J. Biol. Chem. 1985 (260) 279-287.
McCawley et al. "Matrix metalloproteinases: they're not just for matrix anymore!" Curr. Opinion Cell Biol. 2001 (13) 534-540.
Melcher et al. "Plasmid vectors with a 5'-hybrid intron facilitate high-level glycoprotein expression in CHO-cells" Biochimica et Biophysica Acta. 2002 (1575) 49-53.
Munns et al. "Vitamin K-dependent synthesis and modification of precursor prothrombin in cultured H-35 hepatoma cells" Proc. Natl. Acad. Sci. 1976 (73) 2803-2807.
Newby "Matrix metalloproteinases regulate migration, proliferation, and death of vascular smooth muscle cells by degrading matrix and non-matrix substrates" Cardiovascular Res. 2006 (69) 614-624.
Nishida et al. "cDNA cloning and deduced amino acid sequence of prothrombin activator (ecarin) from Kenyan *Echis carinatus* venom" Biochem. 1995 (34) 1771-1778.
Pei et al. "Expression, isolation, and characterization of an active site (serine 528-alanine) mutant of recombinant bovine prothrombin" J. Biol. Chem. 1991 (266) 9598-9604.
Pejler et al. "Thrombin is Inactivated by Mast Cell Secretory Granule Chymase" J. Biol. Chem. 1993 (268) 11817-11822.
Rehemtulla et al. "In vitro and in vivo functional characterization of bovine vitamin K-dependent γ-carboxylase expressed in Chinese hamster ovary cells" Proc. Natl. Acad. Sci. 1993 (90) 4611-4615.
Robertson "Genes Encoding Vitamin-K Epoxide Reductase Are Present in *Drosophila* and Trypanosomatid Protists" Genetics. 2004 (168) 1077-1080.
Roddie at al. "Haemostasis and thrombosis: Recombinant coagulation factors" Blood Reviews. 1997 (11) 169-177.
Rost et al. "Mutations in *VKORC1* cause warfarin resistance and multiple coagulation factor deficiency type 2" Nature. 2004 (427) 537-541.
Rouet et al. "A Potent Enhancer Made of Clustered Liver-specified Elements in the Transcription Control Sequences of Human α1-Microglobulin/Bikunin Gene" The Journal of Biological Chemistry. 1992 (267) 20765-20773.
Russo et al. "Biologically active recombinant prothrombin and antithrombin III expressed in a human hepatoma/vaccinia virus system" Biotechnology and Applied Biochemistry. 1991 (14) 222-223.
Russo et al. "Stable expression and purification of a secreted human recombinant prethrombin-2 and its activation to thrombin" Protein Expression and Purification. 1997 (10) 214-225.
Sadler "K is for koagulation" Nature. 2004 (427) 493-494.
Scharrer "The Need for Highly Purified Products to Treat Hemophilia B" Acta Haematol. 1995 (94) 2-7.
Scharrer et al. "Products used to treat hemophilia: evolution of treatment for hemophilia A and B" in: Lee et al. eds., Tektbook of Hemophilia (New York, Blackwell, 2005), Ch. 23, pp. 131-135.
Seffernick et al. "Melamine Deaminase and Atrazine Chlorohydrolase: 98 Percent Identical but Functionally Different" J. Bacteriol. 2001 (183) 2405-2410.
Slimko et al. "Codon optimization of *Caenorhabditis* elegans G1uCl ion channel genes for mammalian cells dramatically improves expression levels" J. Neuroscience Methods. 2003 (124) 75-81.
Stanley et al. "The propeptides of the vitamin K-dependent proteins possess different affinities for the vitamin K-dependent carboxylase" J. Biol. Chem. 1999 (274) 16940-16944.
Strausberg et al. "Generation and initial analysis of more than 15,000 full-length human and mouse cDNA sequences" PNAS. 2002 (99) 16899-16903.
Sun et al. "Vitamin K epoxide reductase significantly improves carboxylation in a cell line overexpressing factor X" Blood. 2005 (106) 3811-3815.

(56) References Cited

OTHER PUBLICATIONS

Tans et al. "Prothrombin Activation by Snake Venom Proteases" J. Toxicol.-Toxin Reviews. 1993 (12) 155-173.
Umaña et al. "Tetracycline-Regulated Overexpression of Glycosyltransferases in Chinese Hamster Ovary Cells" Biotechnology and Bioengineering. 1999 (65) 542-549.
Vo et al. "Undercarboxylation of recombinant prothrombin revealed by analysis of γ-carboxyglutamic acid using capillary electrophoresis and laser-induced fluorescence" Febs Letters. 1999 (445) 256-260.
Wajih et al. "Engineering of a Recombinant Vitamin K-dependent γ-Carboxylation System with Enhanced γ-Carboxyglutamic Acid Forming Capacity" J. Biol. Chem. 2005 (280) 10540-10547.
Wajih et al. "Increased Production of Functional Recombinant Human Clotting Factor IX by Baby Hamster Kidney Cells Engineered to Overexpress VKORC1, the Vitamin K 2,3-Expoxide-reducing Enzyme of the Vitamin K Cycle" J. Biol. Chem. 2005 (280) 31603-31607.
Wajih et al. "The Inhibitory Effect of Calumenin on the Vitamin K-dependent γ-Carboxylation System" J. Biol. Chem. 2004 (279) 25276-25283.
Walker at al., "On a potential global role for vitamin K-dependent γ-carboxylation in animal systems" J. Biol. Chem. 2001 (276) 7769-7774.
Wallin et al. "Vitamin K-dependent Carboxylation and Vitamin K Metabolism in Liver" J. Clin. Invest. 1985 (76) 1879-1884.
Wallin et al. "Vitamin K 2,3-epoxide reductase and the vitamin K-dependent γ-carboxylation system" Thrombosis Research. 2003 (108) 221-226.
Wang et al. "The Growth Inhibitory Effects of Vitamins K and Their Actions on Gene Expression" Hepatology. 1995 (22) 876-882.
Whisstock et al. "Prediction of protein function from protein sequence and structure" Q. Rev. Biophysics. 2003 (36) 307-340.
Witkowski et al. "Conversion of β-Ketoacyl Synthase to a Malonyl Decarboxylase by Replacement of the Active-Site Cysteine with Glutamine" Biochemistry. 1999 (38) 11643-11650.
Wu et al. "Cloning and expression of the cDNA for human γ-glutamyl carboxylase" Science. 1991 (254) 1634-1636.
Wu et al. "N-Glycosylation contributes to the intracellular stability of prothrombin precursors in the endoplasmic reticulum" Thrombosis Research. 1999 (96) 91-98.
Yonemura et al. "Preparation of recombinant α-thrombin: high-level expression of recombinant human prethrombin-2 and its activation by recombinant ecarin" J. Biochem. 2004 (135) 577-582.
Zhang et al. "Relative Promoter Strengths in Four Human Prostate Cancer Cell Lines Evaluated by Particle Bombardment-Mediated Gene Transfer" The Prostate. 2002 (51) 286-292.
PCT Written Opinion for Application No. PCT/SE2008/050836, dated Jan. 21, 2010, 10 pages.
Nucleotide sequence of human prothrombin (EBI accession No. AJ972449), last modified Oct. 21, 2008, 8 pages.
Amino acid sequence for wild type ecarin (EBI accession No. Q90495), last modified Jan. 19, 2010, 5 pages.
USPTO Restriction Requirement in U.S. Appl. No. 10/964,888, mailed Aug. 9, 2006, 10 pages.
Fish & Richardson P.C., Amendment in Reply to Restriction Requirement dated Aug. 9, 2006 in U.S. Appl. No. 10/964,888, filed Feb. 6, 2007, 11 pages.
USPTO Non-Final Office Action in U.S. Appl. No. 10/964,888, mailed Apr. 19, 2007, 17 pages.
Fish & Richardson P.C., Amendment in Reply to Action dated Apr. 19, 2007 in U.S. Appl. No. 10/964,888, filed Oct. 18, 2007, 26 pages.
USPTO Non-Final Office Action in U.S. Appl. No. 10/964,888, mailed Jan. 28, 2008, 29 pages.
Fish & Richardson P.C., Amendment in Reply to Action dated Jan. 28, 2008 in U.S. Appl. No. 10/964,888, filed Apr. 28, 2008, 22 pages.
USPTO Final Office Action in U.S. Appl. No. 10/964,888, mailed Apr. 3, 2009, 6 pages.
Fish & Richardson P.C., Amendment in Reply to Action dated Apr. 3, 2009 in U.S. Appl. No. 10/964,888, filed Jun. 17, 2009, 15 pages.
USPTO Non-Final Office Action in U.S. Appl. No. 10/964,888, mailed Aug. 21, 2009, 5 pages.
Fish & Richardson P.C., Amendment in Reply to Action dated Aug. 21, 2009 in U.S. Appl. No. 10/964,888, filed Nov. 10, 2009, 17 pages.
USPTO Non-Final Office Action in U.S. Appl. No. 10/964,888, mailed Jan. 27, 2010, 9 pages.
Fish & Richardson P.C., Amendment in Reply to Non-Final Action of Jan. 27, 2010 in U.S. Appl. No. 10/964,888, filed Apr. 14, 2010, 15 pages.
USPTO Notice of Allowance in U.S. Appl. No. 10/964,888, mailed Jul. 20, 2010, 6 pages.
Fish & Richardson P.C., Response to Notice of Allowance of Jul. 20, 2010 in U.S. Appl. No. 10/964,888, filed Oct. 20, 2010, 3 pages.
USPTO Restriction Requirement in U.S. Appl. No. 11/572,870, mailed Apr. 2, 2009, 5 pages.
Fish & Richardson P.C., Response to Restriction Requirement and Preliminary Amendment dated Apr. 2, 2009 in U.S. Appl. No. 11/572,870, filed Sep. 25, 2009, 16 pages.
USPTO Non-Final Office Action in U.S. Appl. No. 11/572,870, mailed Jan. 26, 2010, 18 pages.
Fish & Richardson P.C., Amendment in Reply to Action of Jan. 26, 2010 in U.S. Appl. No. 11/572,870, filed May 26, 2010, 21 pages.
USPTO Final Office Action in U.S. Appl. No. 11/572,870, mailed Aug. 6, 2010, 18 pages.
USPTO Restriction Requirement in U.S. Appl. No. 12/167,614, mailed Apr. 6, 2009, 8 pages.
Fish & Richardson P.C., Amendment in Reply to Restriction Requirement dated Apr. 6, 2009 in U.S. Appl. No. 12/167,614, filed Aug. 4, 2009, 9 pages.
USPTO Non-Final Office Action in U.S. Appl. No. 12/167,614, mailed Sep. 29, 2009, 19 pages.
Fish & Richardson P.C., Amendment in Reply to Action of Sep. 29, 2009 in U.S. Appl. No. 12/167,614, filed Feb. 26, 2010, 26 pages.
USPTO Non-Final Office Action in U.S. Appl. No. 12/167,614, mailed May 25, 2010, 47 pages.
Extended European Search Report issued in EP10185166.5 on Jan. 27, 2011 (5 pages).
Fish & Richardson P.C., Amendment in Reply to Action of Feb. 3, 2012 in U.S. Appl. No. 13/167,134, filed May 3, 2012, 5 pages.
Fish & Richardson P.C., Amendment in Reply to Action of May 25, 2010 in U.S. Appl. No. 12/167,614, filed Nov. 23, 2010, 28 pages.
Fish & Richardson P.C., RCE and Amendment in Reply to Action of Aug. 6, 2010 in U.S. Appl. No. 11/572,870, filed Feb. 7, 2011, 16 pages.
Fish & Richardson P.C., Request for Continued Examination and Amendment in Reply to Action of Jan. 24, 2011 in U.S. Appl. No. 12/167,614, filed Jul. 21, 2011, 15 pages.
Fish & Richardson P.C., Response to Notice of Allowance of Feb. 28, 2012 in U.S. Appl. No. 12/167,614, filed May 25, 2012, 2 pages.
Fish & Richardson P.C., Response to Notice of Allowance of Jun. 29, 2012 in U.S. Appl. No. 13/167,134, filed Sep. 28, 2012, 4 pages.
Fish & Richardson P.C., Response to Notice of Allowance of Mar. 24, 2011 in U.S. Appl. No. 11/572,870, filed Jun. 23, 2011, 2 pages.
International Preliminary Report on Patentability issued in PCT/SE2004/001453 on Apr. 18, 2006 (6 pages).
International Search Report issued in PCT/SE2004/001453 on Jan. 21, 2005 (3 pages).
USPTO Notice of Allowance in U.S. Appl. No. 11/572,870, mailed Mar. 24, 2011 (8 pages).
USPTO Notice of Allowance in U.S. Appl. No. 13/167,134, mailed Jun. 29, 2012 (8 pages).
USPTO Final Office Action in U.S. Appl. No. 12/167,614, mailed Jan. 24, 2011, 52 pages.
USPTO Non-Final Office Action in U.S. Appl. No. 13/524,689, Mailed Nov. 5, 2012, 22 pages.
USPTO Notice of Allowance in U.S. Appl. No. 12/167,614, mailed Feb. 28, 2012, 11 pages.
USPTO Non-Final Office Action in U.S. Appl. No. 13/167,134, mailed Feb. 3, 2012, 5 pages.
USPTO Restriction Requirement in U.S. Appl. No. 13/665,441, Mailed Feb. 22, 2013, 8 pages.

* cited by examiner

SEQUENCE LISTING

```
<160> NUMBER OF SEQ ID NOS: 15

<210> SEQ ID NO 1
<211> LENGTH: 7422
<212> TYPE: DNA
<213> ORGANISM: Artificial Sequence
<220> FEATURE:
<223> OTHER INFORMATION: vector

<400> SEQUENCE: 1
gacggatcgg gagatctccc gatccctat ggtcgactct cagtacaatc tgctctgatg      60
ccgcatagtt aagccagtat ctgctccctg cttgtgtgtt ggaggtcgct gagtagtgcg     120
```

```
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgcc ccattgacgc aaatgggcg    780 gtaggcgtgt acggtgggag gtctatataa gcagagctct ctggctaact agagaaccca    840
ctgcttactg gcttatcgaa attaatacga ctcactatag ggagacccaa gctggctagt    900
taagcttggt accgagctcg gatccactag tccagtgtgg tggaattgcc cttattcctc    960
agtgacccag gagctgacac actatggcgc acgtccgagg cttgcagctg cctggctgcc   1020
tggccctggc tgccctgtgt agccttgtgc acagccagca tgtgttcctg gctcctcagc   1080
aagcacggtc gctgctccag cgggtccggc gagccaacac cttcttggag gaggtgcgca   1140
agggcaacct ggagcgagag tgcgtggagg agacgtgcag ctacgaggag gccttcgagg   1200
ctctggagtc ctccacggct acggatgtgt tctgggccaa gtacacagct gtgagacag    1260 cgaggacgcc tcgagataag cttgctgcat gtctggaagg taactgtgct gagggtctgg   1320
gtacgaacta ccgagggcat gtgaacatca cccggtcagg cattgagtgc cagctatgga   1380
ggagtcgcta cccacataag cctgaaatca actccactac ccatcctggg gccgacctac   1440
aggagaattt ctgccgcaac cccgacagca gcaccacggg accctggtgc tacactacag   1500
accccaccgt gaggaggcag gaatgcagca tccctgtctg tggccaggat caagtcactg   1560
tagcgatgac tccacgctcc gaaggctcca gtgtgaatct gtcacctcca ttggagcagt   1620
gtgtccctga tcgggggcag cagtaccagg ggcgcctggc ggtgaccaca catgggctcc   1680
cctgcctggc ctgggccagc gcacaggcca aggccctgag caagcaccag gacttcaact   1740
cagctgtgca gctggtggag aacttctgcc gcaacccaga cggggatgag gagggcgtgt   1800
ggtgctatgt ggccgggaag cctggcgact ttgggtactg cgacctcaac tattgtgagg   1860
aggccgtgga ggaggagaca ggagatgggc tggatgagga ctcagacagg gccatcgaag   1920
ggcgtaccgc caccagtgag taccagactt tcttcaatcc gaggacctttt ggctcgggag   1980 aggcagactg tgggctgcga cctctgttcg agaagaagtc gctggaggac aaaaccgaaa   2040
gagagctcct ggaatcctac atcgacgggc gcattgtgga gggctcggat gcagagatcg   2100
gcatgtcacc ttggcaggtg atgctttttc ggaagagtcc caggagctg ctgtgtgggg   2160 ccagcctcat cagtgaccgc tgggtcctca ccgccgccca ctgcctcctg taccccgcct   2220
gggacaagaa cttcaccgag aatgaccttc tggtgcgcat tggcaagcac tcccgcacca   2280
ggtacgagcg aaacattgaa aagatatcca tgttggaaaa gatctacatc caccccaggt   2340
acaactggcg ggagaacctg gaccgggaca ttgccctgat gaagctgaag agcctgttg    2400 ccttcagtga ctacattcac cctgtgtgtc tgcccgacag ggacacgca gccagcttgc    2460 tccaggctgg atacaagggg cgggtgacag gctggggcaa cctgaaggag acgtggacag   2520
```

```
ccaacgttgg taaggggcag cccagtgtcc tgcaggtggt gaacctgccc attgtggagc    2580
ggccggtctg caaggactcc acccggatcc gcatcactga caacatgttc tgtgctggtt    2640
acaagcctga tgaagggaaa cgaggggatg cctgtgaagg tgacagtggg ggacccttg    2700 tcatgaagag ccccttaac aaccgctggt atcaaatggg catcgtctca tggggtgaag    2760
gctgtgaccg ggatgggaaa tatggcttct acacacatgt gttccgcctg aagaagtgga    2820
tacagaaggt cattgatcag tttggagagt agaagggcaa ttctgcagat atccagcaca    2880
gtggcggccg ctcgagtcta gagggcccgc ggttcgaagg taagcctatc cctaaccctc    2940
tcctcggtct cgattctacg cgtaccggtc atcatcacca tcaccattga gtttaaaccc    3000
gctgatcagc ctcgactgtg ccttctagtt gccagccatc tgttgtttgc cctcccccg    3060 tgccttcctt gaccctggaa ggtgccactc ccactgtcct ttcctaataa aatgaggaaa    3120
ttgcatcgca ttgtctgagt aggtgtcatt ctattctggg gggtggggtg gggcaggaca    3180 gcaagggga ggattgggaa gacaaatagca ggcatgctgg ggatgcggtg ggctctatgg    3240
cttctgaggc ggaaagaacc agctggggct ctaggggta tccccacgcg ccctgtagcg    3300
gcgcattaag cgcggcgggt gtggtggtta cgcgcagcgt gaccgctaca cttgccagcg    3360
ccctagcgcc cgctcctttc gctttcttcc cttcctttct cgccacgttc gccggctttc    3420
cccgtcaagc tctaaatcgg ggcatccctt tagggttccg atttagtgct ttacggcacc    3480 tcgacccaa aaaacttgat tagggtgatg gttcacgtag tgggccatcg ccctgataga    3540 cggttttcg ccctttgacg ttggagtcca cgttctttaa tagtggactc ttgttccaaa    3600
ctggaacaac actcaaccct atctcggtct attctttga tttataaggg attttgggga    3660
tttcggccta ttggttaaaa aatgagctga tttaacaaaa atttaacgcg aattaattct    3720
gtggaatgtg tgtcagttag ggtgtggaaa gtccccaggc tccccaggca ggcagaagta    3780
tgcaaagcat gcatctcaat tagtcagcaa ccaggtgtgg aaagtcccca ggctccccag    3840
caggcagaag tatgcaaagc atgcatctca attagtcagc aaccatagtc cgcccctaa    3900 ctccgcccat cccgccccta actccgccca gttccgccca ttctccgccc catggctgac    3960
taattttttt tatttatgca gaggccgagg ccgcctctgc ctctgagcta ttccagaagt    4020
agtgaggagg cttttttgga ggcctaggct tttgcaaaaa gctcccggga gcttgtatat    4080
ccattttcgg atctgatcaa gagacaggat gaggatcgtt tcgcatgatt gaacaagatg    4140
gattgcacgc aggttctccg gccgcttggg tggagaggct attcggctat gactgggcac    4200
aacagacaat cggctgctct gatgccgccg tgttccggct gtcagcgcag ggcgcccgg    4260 ttcttttgt caagaccgac ctgtccggtg ccctgaatga actgcaggac gaggcagcgc    4320
ggctatcgtg gctggccacg acgggcgttc cttgcgcagc tgtgctcgac gttgtcactg    4380
aagcgggaag ggactggctg ctattgggcg aagtgccggg gcaggatctc ctgtcatctc    4440
accttgctcc tgccgagaaa gtatccatca tggctgatgc aatgcggcgg ctgcatacgc    4500
ttgatccggc tacctgccca ttcgaccacc aagcgaaaca tcgcatcgag cgagcacgta    4560
ctcggatgga agccggtctt gtcgatcagg atgatctgga cgaagagcat caggggctcg    4620
cgccagccga actgttcgcc aggctcaagg cgcgcatgcc cgacggcgag gatctcgtcg    4680
tgacccatgg cgatgcctgc ttgccgaata tcatggtgga aaatggccgc ttttctggat    4740
tcatcgactg tggccggctg ggtgtggcgg accgctatca ggacatagcg ttggctaccc    4800
gtgatattgc tgaagagctt ggcggcgaat gggctgaccg cttcctcgtg ctttacggta    4860
tcgccgctcc cgattcgcag cgcatcgcct tctatcgcct tcttgacgag ttcttctgag    4920
```

```
cgggactctg gggttcgcga aatgaccgac caagcgacgc ccaacctgcc atcacgagat    4980
ttcgattcca ccgccgcctt ctatgaaagg ttgggcttcg gaatcgtttt ccgggacgcc    5040
ggctggatga tcctccagcg cggggatctc atgctggagt tcttcgccca ccccaacttg    5100
tttattgcag cttataatgg ttacaaataa agcaatagca tcacaaattt cacaaataaa    5160 gcatttttt cactgcattc tagttgtggt ttgtccaaac tcatcaatgt atcttatcat    5220
gtctgtatac cgtcgacctc tagctagagc ttggcgtaat catggtcata gctgtttcct    5280
gtgtgaaatt gttatccgct cacaattcca cacaacatac gagccggaag cataaagtgt    5340
aaagcctggg gtgcctaatg agtgagctaa ctcacattaa ttgcgttgcg ctcactgccc    5400
gctttccagt cgggaaacct gtcgtgccag ctgcattaat gaatcggcca acgcgcgggg    5460
agaggcggtt tgcgtattgg gcgctcttcc gcttcctcgc tcactgactc gctgcgctcg    5520
gtcgttcggc tgcggcgagc ggtatcagct cactcaaagg cggtaatacg gttatccaca    5580
gaatcagggg ataacgcagg aaagaacatg tgagcaaaag gccagcaaaa ggccaggaac    5640
cgtaaaaagg ccgcgttgct ggcgtttttc cataggctcc gcccccctga cgagcatcac    5700
aaaaatcgac gctcaagtca gaggtggcga acccgacag gactataaag ataccaggcg    5760
tttccccctg gaagctccct cgtgcgctct cctgttccga ccctgccgct taccggatac    5820
ctgtccgcct ttctcccttc gggaagcgtg gcgctttctc aatgctcacg ctgtaggtat    5880
ctcagttcgg tgtaggtcgt tcgctccaag ctgggctgtg tgcacgaacc ccccgttcag    5940
cccgaccgct gcgccttatc cggtaactat cgtcttgagt ccaacccggt aagacacgac    6000
ttatcgccac tggcagcagc cactggtaac aggattagca gagcgaggta tgtaggcggt    6060
gctacagagt tcttgaagtg gtggcctaac tacggctaca ctagaaggac agtatttggt    6120
atctgcgctc tgctgaagcc agttaccttc ggaaaaagag ttggtagctc ttgatccggc    6180
aaacaaacca ccgctggtag cggtggtttt tttgtttgca agcagcagat tacgcgcaga    6240
aaaaaaggat ctcaagaaga tcctttgatc ttttctacgg ggtctgacgc tcagtggaac    6300
gaaaactcac gttaagggat tttggtcatg agattatcaa aaaggatctt cacctagatc    6360
cttttaaatt aaaaatgaag ttttaaatca atctaaagta tatatgagta aacttggtct    6420
gacagttacc aatgcttaat cagtgaggca cctatctcag cgatctgtct atttcgttca    6480
tccatagttg cctgactccc cgtcgtgtag ataactacga tacgggaggg cttaccatct    6540
ggccccagtg ctgcaatgat accgcgagac ccacgctcac cggctccaga tttatcagca    6600
ataaaccagc cagccggaag ggccgagcgc agaagtggtc ctgcaacttt atccgcctcc    6660
atccagtcta ttaattgttg ccgggaagct agagtaagta gttcgccagt taatagtttg    6720
cgcaacgttg ttgccattgc tacaggcatc gtggtgtcac gctcgtcgtt tggtatggct    6780
tcattcagct ccggttccca acgatcaagg cgagttacat gatcccccat gttgtgcaaa    6840
aaagcggtta gctccttcgg tcctccgatc gttgtcagaa gtaagttggc cgcagtgtta    6900
tcactcatgg ttatggcagc actgcataat tctcttactg tcatgccatc cgtaagatgc    6960
ttttctgtga ctggtgagta ctcaaccaag tcattctgag aatagtgtat gcggcgaccg    7020
agttgctctt gcccggcgtc aatacgggat aataccgcgc cacatagcag aactttaaaa    7080
gtgctcatca ttggaaaacg ttcttcgggg cgaaaactct caaggatctt accgctgttg    7140
agatccagtt cgatgtaacc cactcgtgca cccaactgat cttcagcatc ttttactttc    7200
accagcgttt ctgggtgagc aaaaacagga aggcaaaatg ccgcaaaaaa gggaataagg    7260
gcgacacgga aatgttgaat actcatactc ttcctttttc aatattattg aagcatttat    7320
```

-continued

```
cagggttatt gtctcatgag cggatacata tttgaatgta tttagaaaaa taaacaaata      7380
ggggttccgc gcacatttcc ccgaaaagtg ccacctgacg tc                          7422

<210> SEQ ID NO 2
<211> LENGTH: 10139
<212> TYPE: DNA
<213> ORGANISM: Artificial Sequence
<220> FEATURE:
<223> OTHER INFORMATION: vector

<400> SEQUENCE: 2
gacggatcgg gagatctccc gatcccctat ggtgcactct cagtacaatc tgctctgatg        60
ccgcatagtt aagccagtat ctgctccctg cttgtgtgtt ggaggtcgct gagtagtgcg       120
cgagcaaaat ttaagctaca acaaggcaag gcttgaccga caattgcatg aagaatctgc       180
ttagggttag gcgttttgcg ctgcttcgcg atgtacgggc cagatatacg cgttgacatt       240
gattattgac tagttattaa tagtaatcaa ttacggggtc attagttcat agcccatata       300
tggagttccg cgttacataa cttacggtaa atggcccgcc tggctgaccg cccaacgacc       360
cccgcccatt gacgtcaata atgacgtatg ttcccatagt aacgccaata gggactttcc       420
attgacgtca atgggtggag tatttacggt aaactgccca cttggcagta catcaagtgt       480
atcatatgcc aagtacgccc cctattgacg tcaatgacgg taaatggccc gcctggcatt       540
atgcccagta catgacctta tgggactttc ctacttggca gtacatctac gtattagtca       600
tcgctattac catggtgatg cggttttggc agtacatcaa tgggcgtgga tagcggtttg       660
actcacgggg atttccaagt ctccacccca ttgacgtcaa tgggagtttg ttttggcacc       720
aaaatcaacg ggactttcca aaatgtcgta acaactccgc cccattgacg caaatgggcg       780
gtaggcgtgt acggtgggag gtctatataa gcagagctct ctggctaact agagaaccca       840
ctgcttactg gcttatcgaa attaatacga ctcactatag ggagacccaa gctggctagc       900
gtttaaactt aagcttggta ccgagctcgg atccactagt ccagtgtggt ggaattgccc       960
ttattcctca gtgacccagg agctgacaca ctatggcgca cgtccgaggc ttgcagctgc      1020
ctggctgcct ggccctggct gccctgtgta gccttgtgca cagccagcat gtgttcctgg      1080
ctcctcagca agcacggtcg ctgctccagc gggtccggcg agccaacacc ttcttggagg      1140
aggtgcgcaa gggcaacctg gagcgagagt gcgtggagga cgtgcagc tacgaggagg        1200 ccttcgaggc tctggagtcc tccacaggcta cggatgtgtt ctgggccaag tacacagctt      1260
gtgagacagc gaggacgcct cgagataagc ttgctgcatg tctggaaggt aactgtgctg      1320
agggtctggg tacgaactac cgagggcatg tgaacatcac ccggtcaggc attgagtgcc      1380
agctatggag gagtcgctac ccacataagc ctgaaatcaa ctccactacc catcctgggg      1440
ccgacctaca ggagaatttc tgccgcaacc ccgacagcag caccacggga ccctggtgct      1500
acactacaga ccccaccgtg aggaggcagg aatgcagcat ccctgtctgt ggccaggatc      1560
aagtcactgt agcgatgact ccacgctccg aaggctccag tgtgaatctg tcacctccat      1620
tggagcagtg tgtccctgat cggggggcagc agtaccaggg gcgcctggcg gtgaccacac      1680
atgggctccc ctgcctggcc tgggccagcg cacaggccaa ggccctgagc aagcaccagg      1740
acttcaactc agctgtgcag ctggtggaga acttctgccg caacccagac ggggatgagg      1800
agggcgtgtg gtgctatgtg gccgggaagc ctggcgactt ggggtactgc gacctcaact      1860
attgtgagga ggccgtggag gaggagacag gagatgggct ggatgaggac tcagacaggg      1920
ccatcgaagg gcgtaccgcc accagtgagt accagactt cttcaatccg aggacctttg      1980
```

```
gctcgggaga ggcagactgt gggctgcgac ctctgttcga gaagaagtcg ctggaggaca    2040
aaaccgaaag agagctcctg gaatcctaca tcgacgggcg cattgtggag ggctcggatg    2100
cagagatcgg catgtcacct tggcaggtga tgcttttccg gaagagtccc caggagctgc    2160
tgtgtggggc cagcctcatc agtgaccgct gggtcctcac cgccgcccac tgcctcctgt    2220
acccgccctg ggacaagaac ttcaccgaga atgaccttct ggtgcgcatt ggcaagcact    2280
cccgcaccag gtacgagcga acattgaaa agatatccat gttggaaaag atctacatcc    2340
accccaggta caactggcgg gagaacctgg accgggacat tgccctgatg aagctgaaga    2400
agcctgttgc cttcagtgac tacattcacc ctgtgtgtct gcccgacagg gagacggcag    2460
ccagcttgct ccaggctgga tacaagggc gggtgacagg ctgggcaac ctgaaggaga     2520 cgtggacagc caacgttggt aagggcagc ccagtgtcct gcaggtggtg aacctgccca     2580
ttgtggagcg gccggtctgc aaggactcca cccggatccg catcactgac aacatgttct    2640
gtgctggtta caagcctgat gaagggaaac gaggggatgc ctgtgaaggt gacagtgggg    2700 gacccttttgt catgaagagc ccctttaaca accgctggta tcaaatgggc atcgtctcat    2760
ggggtgaagg ctgtgaccgg gatgggaaat atggcttcta cacacatgtg ttccgcctga    2820
agaagtggat acagaaggtc attgatcagt ttggagagta aagggcaat tctgcagata     2880 tccagcacag tggcggccgc tcgagtctag agggcccgtt taaacccgct gatcagcctc    2940
gactgtgcct tctagttgcc agccatctgt tgtttgcccc tcccccgtgc cttccttgac    3000 cctgaaggt gccactccca ctgtcctttc ctaataaaat gaggaaattg catcgcattg     3060
tctgagtagg tgtcattcta ttctgggggg tggggtgggg caggacagca agggggagga    3120
ttgggaagac aatagcaggc atgctgggga tgcggtgggc tctatggctt ctgaggcgga    3180
aagaaccagc tggggctcta gggggtatcc ccacgcgccc tgtagcggcg cattaagcgc    3240
ggcgggtgtg gtggttacgc gcagcgtgac cgctacactt gccagcgccc tagcgcccgc    3300
tcctttcgct ttcttccctt cctttctcgc cacgttcgcc ggctttcccc gtcaagctct    3360
aaatcggggg ctccctttag ggttccgatt tagtgcttta cggcaccttc gaccccaaaa    3420
aacttgatta gggctgtgga atgtgtgtca gttagggtgt ggaaagtccc caggctcccc    3480
agcaggcaga agtatgcaaa gcatgcatct caattagtca gcaaccaggt gtggaaagtc    3540
cccaggctcc ccagcaggca gaagtatgca aagcatgcat ctcaattagt cagcaaccat    3600
agtcccgccc ctaactccgc ccatcccgcc cctaactccg cccagttccg cccattctcc    3660
gccccatggc tgactaattt ttttttattta tgcagaggcc gaggccgcct cggcctctga    3720
gctattccag aagtagtgag gaggcttttt tggaggccta ggcttttgca aaaagctctc    3780
tggctaacta gagaacccac tgcttactgg cttatcgaaa ttaatacgac tcactatagg    3840
gagacccaag ctggctagcg tttaaactta agcttggtac cgagctcgga tccactagtc    3900
cagtgtggtg gaattgccct ttccgcagag caatggcggt gtctgccggg tccgcgcgga    3960
cctcgcccag ctcagataaa gtacagaaag acaaggctga actgatctca gggcccaggc    4020
aggacagccg aatagggaaa ctcttgggtt ttgagtggac agatttgtcc agttggcgga    4080
ggctggtgac cctgctgaat cgaccaacgg accctgcaag cttagctgtc tttcgttttc    4140
tttttgggtt cttgatggtg ctagacattc cccaggagcg ggggctcagc tctctggacc    4200
ggaaatacct tgatgggctg gatgtgtgcc gcttcccctt gctggatgcc ctacgcccac    4260
tgccacttga ctgatgtat cttgtctaca ccatcatgtt tctgggggca ctgggcatga     4320
tgctgggcct gtgctaccgg ataagctgtg tgttattcct gctgccatac tggtatgtgt    4380
```

```
ttctcctgga caagacatca tggaacaacc actcctatct gtatgggttg ttggcctttc    4440
agctaacatt catggatgca aaccactact ggtctgtgga cggtctgctg aatgcccata    4500
ggaggaatgc ccacgtgccc ctttggaact atgcagtgct ccgtggccag atcttcattg    4560
tgtacttcat tgcgggtgtg aaaaagctgg atgcagactg ggttgaaggc tattccatgg    4620
aatatttgtc ccggcactgg ctcttcagtc ccttcaaact gctgttgtct gaggagctga    4680
ctagcctgct ggtcgtgcac tggggtgggc tgctgcttga cctctcagct ggtttcctgc    4740
tcttttttga tgtctcaaga tccattggcc tgttctttgt gtcctacttc cactgcatga    4800
attcccagct tttcagcatt ggtatgttct cctacgtcat gctggccagc agccctctct    4860
tctgctcccc tgagtggcct cggaagctgg tgtcctactg cccccgaagg ttgcaacaac    4920
tgttgcccct caaggcagcc cctcagccca gtgtttcctg tgtgtataag aggagccggg    4980
gcaaaagtgg ccagaagcca gggctgcgcg atcagctggg agctgccttc accctgctct    5040
acctcctgga gcagctattc ctgccctatt ctcattttct cacccagggc tataacaact    5100
ggacaaatgg gctgtatggc tattcctggg acatgatggt gcactcccgc tcccaccagc    5160
acgtgaagat cacctaccgt gatggccgca ctggcgaact gggctacctt aaccctgggg    5220
tatttacaca gagtcggcga tggaaggatc atgcagacat gctgaagcaa tatgccactt    5280
gcctgagccg cctgcttccc aagtataatg tcactgagcc ccagatctac tttgatattt    5340
gggtctccat caatgaccgc ttccagcaga ggattttga ccctcgtgtg gacatcgtgc    5400
aggccgcttg gtcacccttt cagcgcacat cctgggtgca accactcttg atggacctgt    5460
ctccctggag ggccaagtta caggaaatca agagcagcct agacaaccac actgaggtgg    5520
tcttcattgc agatttccct ggactgcact tggagaattt tgtgagtgaa gacctgggca    5580
acactagcat ccagctgctg caggggggaag tgactgtgga gcttgtggca gaacagaaga    5640 accagagctct tcgagaggga gaaaaaatgc agttgcctgc tggtgagtac cataaggtgt    5700
atacgacatc acctagcccct tcttgctaca gtacgtctca tgtcaacact acagagcttg    5760
cactggagca agacctggca tatctgcaag aattaaagga aaaggtggag aatgaaagtg    5820
aaacagggcc tctaccccca gagctgcagc ctctgttgga aggggaagta aaaggggcc    5880 ctgagccaac acctctggtt cagaccttc ttagacgcca acaaaggctc caggagattg    5940
aacgccggcg aaatactcct ttccatgagc gattcttccg cttcttgttg cgaaagctct    6000
atgtctttcg ccgcagcttc ctgatgactt gtatctcact tcgaaatctg atattaggcc    6060
gtccttccct ggagcagctg gcccaggagg tgacttatgc aaacttgaga ccctttgagg    6120
cagttggaga actgaatccc tcaaacacgg attcttcaca ttctaatcct cctgagtcaa    6180
atcctgatcc tgtccactca gagttctgaa ggggccaga tgttggaagg gcaattcgag    6240
tctagagggc ccgccctgat agacggtttt tcgccctttg acgttggagt ccacgttctt    6300
taatagtgga ctcttgttcc aaactggaac aacactcaac cctatctcgg tctattcttt    6360
tgatttataa gggattttgc cgatttcggc ctattggtta aaaaatgagc tgatttaaca    6420
aaaatttaac gcgaattaat tctgtggaat gtgtgtcagt tagggtgtgg aaagtcccca    6480
ggctccccag caggcagaag tatgcaaagc atgcatctca attagtcagc aaccaggtgt    6540
ggaaagtccc caggctcccc agcaggcaga agtatgcaaa gcatgcatct caattagtca    6600
gcaaccatag tcccgcccct aactccgccc atcccgcccc taactccgcc cagttccgcc    6660
cattctccgc cccatggctg actaatttt tttatttatg cagaggccga ggccgcctct    6720
gcctctgagc tattccagaa gtagtgagga ggcttttttg gaggcctagg cttttgcaaa    6780
```

```
aagctcccgg gagcttgtat atccattttc ggatctgatc aagagacagg atgaggatcg    6840
tttcgcatga ttgaacaaga tggattgcac gcaggttctc cggccgcttg ggtggagagg    6900
ctattcggct atgactgggc acaacagaca atcggctgct ctgatgccgc cgtgttccgg    6960
ctgtcagcgc aggggcgccc ggttcttttt gtcaagaccg acctgtccgg tgccctgaat    7020
gaactgcagg acgaggcagc gcggctatcg tggctggcca cgacgggcgt tccttgcgca    7080
gctgtgctcg acgttgtcac tgaagcggga agggactggc tgctattggg cgaagtgccg    7140
gggcaggatc tcctgtcatc tcaccttgct cctgccgaga agtatccat catggctgat    7200 gcaatgcggc ggctgcatac gcttgatccg gctacctgcc cattcgacca ccaagcgaaa    7260
catcgcatcg agcgagcacg tactcggatg aagccggtc ttgtcgatca ggatgatctg    7320
gacgaagagc atcagggct cgcgccagcc gaactgttcg ccaggctcaa ggcgcgcatg    7380
cccgacggcg aggatctcgt cgtgacccat ggcgatgcct gcttgccgaa tatcatggtg    7440
gaaaatggcc gcttttctgg attcatcgac tgtggccggc tgggtgtggc ggaccgctat    7500
caggacatag cgttggctac ccgtgatatt gctgaagagc ttggcggcga atgggctgac    7560
cgcttcctcg tgctttacgg tatcgccgct cccgattcgc agcgcatcgc cttctatcgc    7620
cttcttgacg agttcttctg agcgggactc tggggttcga atgaccgac caagcgacgc    7680 ccaacctgcc atcacgagat tcgattcca ccgccgcctt ctatgaaagg ttgggcttcg    7740
gaatcgtttt ccgggacgcc ggctggatga tcctccagcg cggggatctc atgctggagt    7800
tcttcgccca ccccaacttg tttattgcag cttataatgg ttacaaataa agcaatagca    7860
tcacaaattt cacaaataaa gcattttttt cactgcattc tagttgtggt ttgtccaaac    7920
tcatcaatgt atcttatcat gtctgtatac cgtcgacctc tagctagagc ttggcgtaat    7980
catggtcata gctgtttcct gtgtgaaatt gttatccgct cacaattcca cacaacatac    8040
gagccggaag cataaagtgt aaagcctggg gtgcctaatg agtgagctaa ctcacattaa    8100
ttgcgttgcg ctcactgccc gctttccagt cgggaaacct gtcgtgccag ctgcattaat    8160
gaatcggcca acgcgcgggg agaggcggtt tgcgtattgg gcgctcttcc gcttcctcgc    8220
tcactgactc gctgcgctcg gtcgttcggc tgcggcgagc ggtatcagct cactcaaagg    8280
cggtaatacg gttatccaca gaatcagggg ataacgcagg aaagaacatg tgagcaaaag    8340
gccagcaaaa ggccaggaac cgtaaaaagg ccgcgttgct ggcgtttttc cataggctcc    8400
gcccccctga cgagcatcac aaaaatcgac gctcaagtca gaggtggcga aacccgacag    8460
gactataaag ataccaggcg tttccccctg gaagctccct cgtgcgctct cctgttccga    8520
ccctgccgct taccggatac ctgtccgcct ttctcccttc gggaagcgtg gcgctttctc    8580
atagctcacg ctgtaggtat ctcagttcgg tgtaggtcgt tcgctccaag ctgggctgtg    8640
tgcacgaacc ccccgttcag cccgaccgct gcgccttatc cggtaactat cgtcttgagt    8700
ccaacccggt aagacacgac ttatcgccac tggcagcagc cactggtaac aggattagca    8760
gagcgaggta tgtaggcggt gctacagagt tcttgaagtg gtggcctaac tacggctaca    8820
ctagaagaac agtatttggt atctgcgctc tgctgaagcc agttaccttc ggaaaaagag    8880
ttggtagctc ttgatccggc aaacaaacca ccgctggtag cggttttttt gtttgcaagc    8940
agcagattac gcgcagaaaa aaggatctc aagaagatcc tttgatcttt tctacggggt    9000
ctgacgctca gtggaacgaa aactcacgtt aagggatttt ggtcatgaga ttatcaaaaa    9060
ggatcttcac ctagatcctt ttaaattaaa aatgaagttt taaatcaatc taaagtatat    9120
atgagtaaac ttggtctgac agttaccaat gcttaatcag tgaggcacct atctcagcga    9180
```

```
tctgtctatt tcgttcatcc atagttgcct gactccccgt cgtgtagata actacgatac    9240
gggagggctt accatctggc cccagtgctg caatgatacc gcgagaccca cgctcaccgg    9300
ctccagattt atcagcaata aaccagccag ccggaagggc cgagcgcaga agtggtcctg    9360
caactttatc cgcctccatc cagtctatta attgttgccg ggaagctaga gtaagtagtt    9420
cgccagttaa tagtttgcgc aacgttgttg ccattgctac aggcatcgtg gtgtcacgct    9480
cgtcgtttgg tatggcttca ttcagctccg gttcccaacg atcaaggcga gttacatgat    9540
cccccatgtt gtgcaaaaaa gcggttagct ccttcggtcc tccgatcgtt gtcagaagta    9600
agttggccgc agtgttatca ctcatggtta tggcagcact gcataattct cttactgtca    9660
tgccatccgt aagatgcttt tctgtgactg gtgagtactc aaccaagtca ttctgagaat    9720
agtgtatgcg gcgaccgagt tgctcttgcc cggcgtcaat acgggataat accgcgccac    9780
atagcagaac tttaaaagtg ctcatcattg gaaaacgttc ttcggggcga aaactctcaa    9840
ggatcttacc gctgttgaga tccagttcga tgtaacccac tcgtgcaccc aactgatctt    9900
cagcatcttt tactttcacc agcgtttctg ggtgagcaaa aacaggaagg caaaatgccg    9960
caaaaaaggg aataagggcg acacggaaat gttgaatact catactcttc ctttttcaat   10020
attattgaag catttatcag ggttattgtc tcatgagcgg atacatattt gaatgtattt   10080
agaaaaataa acaaataggg gttccgcgca catttccccg aaaagtgcca cctgacgtc   10139

<210> SEQ ID NO 3
<211> LENGTH: 26
<212> TYPE: DNA
<213> ORGANISM: Homo sapiens

<400> SEQUENCE: 3
attcctcagt gacccaggag ctgaca                                           26

<210> SEQ ID NO 4
<211> LENGTH: 42
<212> TYPE: DNA
<213> ORGANISM: Homo sapiens

<400> SEQUENCE: 4
ctactctcca aactgatcaa tgaccttctg tatccacttc tt                         42

<210> SEQ ID NO 5
<211> LENGTH: 23
<212> TYPE: DNA
<213> ORGANISM: Homo sapiens

<400> SEQUENCE: 5
tccgcagagc aatggcggtg tct                                              23

<210> SEQ ID NO 6
<211> LENGTH: 24
<212> TYPE: DNA
<213> ORGANISM: Homo sapiens

<400> SEQUENCE: 6
ccaacatctg gccccttcag aact                                             24

<210> SEQ ID NO 7
<211> LENGTH: 24
<212> TYPE: DNA
<213> ORGANISM: Homo sapiens

<400> SEQUENCE: 7
```
acacctctgg ttcagacctt tctt 24

<210> SEQ ID NO 8
<211> LENGTH: 24
<212> TYPE: DNA
<213> ORGANISM: Homo sapiens

<400> SEQUENCE: 8
aatcgctcat ggaaaggagt attt 24

<210> SEQ ID NO 9
<211> LENGTH: 27
<212> TYPE: DNA
<213> ORGANISM: Homo sapiens

<400> SEQUENCE: 9
caacaaaggc tccaggagat tgaacgc 27

<210> SEQ ID NO 10
<211> LENGTH: 22
<212> TYPE: DNA
<213> ORGANISM: Homo sapiens

<400> SEQUENCE: 10
tggaggacaa aaccgaaaga ga 22

<210> SEQ ID NO 11
<211> LENGTH: 18
<212> TYPE: DNA
<213> ORGANISM: Homo sapiens

<400> SEQUENCE: 11
catccgagcc ctccacaa 18

<210> SEQ ID NO 12
<211> LENGTH: 25
<212> TYPE: DNA
<213> ORGANISM: Homo sapiens

<400> SEQUENCE: 12
ctcctggaat cctacatcga cgggc 25

<210> SEQ ID NO 13
<211> LENGTH: 10238
<212> TYPE: DNA
<213> ORGANISM: Artificial Sequence
<220> FEATURE:
<223> OTHER INFORMATION: vector

<400> SEQUENCE: 13
gacggatcgg gagatctccc gatccccat ggtgcactct cagtacaatc tgctctgatg   60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540

```
atgcccagta catgaccttta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattgccc    960
ttattcctca gtgacccagg agctgacaca ctatggcgca cgtccgaggc ttgcagctgc   1020
ctggctgcct ggccctggct gccctgtgta gccttgtgca cagccagcat gtgttcctgg   1080
ctcctcagca agcacggtcg ctgctccagc gggtccggcg agccaacacc ttcttggagg   1140
aggtgcgcaa gggcaacctg agcgagagt gcgtggagga cgtgcagc tacgaggagg   1200 ccttcgaggc tctggagtcc tccacggcta cggatgtgtt ctgggccaag tacacagctt   1260
gtgagacagc gaggacgcct cgagataagc ttgctgcatg tctggaaggt aactgtgctg   1320
agggtctggg tacgaactac cgagggcatg tgaacatcac ccggtcaggc attgagtgcc   1380
agctatggag gagtcgctac ccacataagc ctgaaatcaa ctccactacc catcctgggg   1440
ccgacctaca ggagaatttc tgccgcaacc ccgacagcag caccacggga ccctggtgct   1500
acactacaga ccccaccgtg aggaggcagg aatgcagcat ccctgtctgt ggccaggatc   1560
aagtcactgt agcgatgact ccacgctccg aaggctccag tgtgaatctg tcacctccat   1620
tggagcagtg tgtccctgat cgggggcagc agtaccaggg gcgcctggcg gtgaccacac   1680
atgggctccc ctgcctggcc tgggccagcg cacaggccaa ggccctgagc aagcaccagg   1740
acttcaactc agctgtgcag ctggtggaga acttctgccg caacccagac ggggatgagg   1800
agggcgtgtg gtgctatgtg gccgggaagc ctggcgactt tgggtactgc gacctcaact   1860
attgtgagga ggccgtggag gaggagacag agatgggct ggatgaggac tcagacaggg   1920
ccatcgaagg gcgtaccgcc accagtgagt accagacttt cttcaatccg aggacctttg   1980
gctcgggaga ggcagactgt gggctgcgac ctctgttcga aagaagtcg ctggaggaca   2040 aaaccgaaag agagctcctg gaatcctaca tcgacgggcg cattgtggag ggctcggatg   2100
cagagatcgg catgtcacct tggcaggtga tgcttttccg gaagagtccc caggagctgc   2160
tgtgtggggc cagcctcatc agtgaccgct gggtcctcac cgccgcccac tgcctcctgt   2220
acccgccctg ggacaagaac ttcaccgaga atgaccttct ggtgcgcatt ggcaagcact   2280
cccgcaccag gtacgagcga acattgaaa agatatccat gttggaaaag atctacatcc   2340
accccaggta caactggcgg gagaacctgg accgggacat gccctgatg aagctgaaga   2400 agcctgttgc cttcagtgac tacattcacc ctgtgtgtct gcccgacagg agacggcag   2460 ccagcttgct ccaggctgga tacaaggggc gggtgacagg ctgggcaac ctgaaggaga   2520 cgtggacagc caacgttggt aaggggcagc ccagtgtcct gcaggtggtg aacctgccca   2580
ttgtggagcg gccggtctgc aaggactcca cccggatccg catcactgac aacatgttct   2640
gtgctggtta caagcctgat gaagggaaac gaggggatgc ctgtgaaggt gacagtgggg   2700
gaccctttgt catgaagagc ccctttaaca accgctggta tcaaatgggc atcgtctcat   2760
ggggtgaagg ctgtgaccgg gatgggaaat atggcttcta cacacatgtg ttccgcctga   2820
agaagtggat acagaaggtc attgatcagt ttggagagta gaagggcaat tctgcagata   2880
tccagcacag tggcggccgc tcggttccta gagggcccgt ttaaacccgc tgatcagcct   2940
```

```
cgactgtgcc ttctagttgc cagccatctg ttgtttgccc ctcccccgtg ccttccttga   3000
ccctggaagg tgccactccc actgtccttt cctaataaaa tgaggaaatt gcatcgcatt   3060
gtctgagtag gtgtcattct attctggggg gtggggtggg gcaggacagc aaggggagg    3120 attgggaaga caatagcagg catgctgggg atgcggtggg ctctatggct tctgaggcgg   3180
aaagaaccag ctggggctct aggggtatc cccacgcgcc ctgtagcggc gcattaagcg    3240
cggcgggtgt ggtggttacg cgcagcgtga ccgctacact tgccagcgcc ctagcgcccg   3300
ctcctttcgc tttcttccct tcctttctcg ccacgttcgc cggctttccc cgtcaagctc   3360
taaatcgggg gctcccttta gggttccgat ttagtgcttt acggcacctc gaccccaaaa   3420
aacttgatta gggtgatggt tcacatcgat gcaatttcct cattttatta ggaaaggaca   3480
gtgggagtgg caccttccag ggtcaaggaa ggcacggggg aggggcaaac aacagatggc   3540
tggcaactag aaggcacagt cgaggctgat cagcgggttt aaacgggccc tctagactcg   3600
aattgcccct tccaacatctg gccccttca gaactctgag tggacaggat caggatttga   3660
ctcaggagga ttagaatgtg aagaatccgt gtttgaggga ttcagttctc caactgcctc   3720
aaagggtctc aagtttgcat aagtcacctc ctgggccagc tgctccaggg aaggacggcc   3780
taatatcaga tttcgaagtg agatacaagt catcaggaag ctgcggcgaa agacatagag   3840
ctttcgcaac aagaagcgga agaatcgctc atggaaagga gtatttcgcc ggcgttcaat   3900
ctcctggagc ctttgttggc gtctaagaaa ggtctgaacc agaggtgttg gctcagggcc   3960
cccttttact tccccttcca acagaggctg cagctctggg ggtagaggcc ctgtttcact   4020
tccattctcc accttttcct ttaattcttg cagatatgcc aggtcttgct ccagtgcaag   4080
ctctgtagtg ttgacataga cgtacatgta gcaagaaggg ctaggtgatg tcgtatacac   4140
cttatggtac tcaccagcag gcaactgcat tttttctccc tctcgaagag tctggttctt   4200
ctgttctgcc acaagctcca cagtcacttc ccctgcagc agctggatgc tagtgttgcc    4260
caggtcttca ctcacaaaat tctccaagtg cagtccaggg aaatctgcaa tgaagaccac   4320
ctcagtgtgg ttgtctaggc tgctcttgat ttcctgtaac ttggccctcc agggagacag   4380
gtccatcaag agtggttgca cccaggatgt gcgctgaaag ggtgaccaag cggcctgcac   4440
gatgtccaca cgagggtcaa aaatcctctg ctggaagcgg tcattgatgg agacccaaat   4500
atcaaagtag atctggggct cagtgacatt atacttggga agcaggcggc tcaggcaagt   4560
ggcatattgc ttcagcatgt ctgcatgatc cttccatcgc cgactctgtg taaataccccc  4620 agggttaagg tagcccagtt cgccagtgcg gccatcacgg taggtgatct tcacgtgctg   4680
gtgggagcgg gagtgcacca tcatgtccca ggaatagcca tacagcccat tgtccagtt    4740 gttatagccc tgggtgagaa aatgagaata gggcaggaat agctgctcca ggaggtagag   4800
cagggtgaag gcagctccca gctgatggcg cagccctggc ttctggccac ttttgccccg   4860
gctcctctta tacacacagg aaacactggg ctgaggggct gccttgaggg gcaacagttg   4920
ttgcaacctt cggggcagt aggacaccag cttccgaggc cactcaggg agcagaagag    4980 agggctgctg gccagcatga cgtaggagaa cataccaatg ctgaaaagct gggaattcat   5040
gcagtggaag taggacacaa agaacaggcc aatggatctt gagacatcaa aaaagagcag   5100
gaaaccagct gagaggtcaa gcagcagccc accccagtgc acgaccagca ggctagtcag   5160
ctcctcagac aacagcagtt tgaagggact gaagagccag tgccgggaca aatattccat   5220
ggaatagcct tcaacccagt ctgcatccag ctttttcaca cccgcaatga agtacacaat   5280
gaagatctgg ccacggagca ctgcatagtt ccaaagggc acgtgggcat tcctcctatg    5340
```

```
ggcattcagc agaccgtcca cagaccagta gtggtttgca tccatgaatg ttagctgaaa    5400
ggccaacaac ccatacagat aggagtggtt gttccatgat gtcttgtcca ggagaaacac    5460
ataccagtat ggcagcagga ataacacaca gcttatccgg tagcacaggc ccagcatcat    5520
gcccagtgcc cccagaaaca tgatggtgta gacaagatac atccagtcaa gtggcagtgg    5580
gcgtagggca tccagcaagg ggaagcggca cacatccagc ccatcaaggt atttccggtc    5640
cagagagctg agccccgct cctggggaat gtctagcacc atcaagaacc caaaagaaa     5700 acgaaagaca gctaagcttg cagggtccgt tggtcgattc agcagggtca ccagcctccg    5760
ccaactggac aaatctgtcc actcaaaacc caagagtttc cctattcggc tgtcctgcct    5820
gggccctgag atcagttcag ccttgtcttt ctgtacttta tctgagctgg gcaggtccg    5880 cgcggacccg gcagacaccg ccattgctct gcggaaaggg caattccacc acactggact    5940
agtggatccg agctcggtac caagcttaag tttaaacgct agccagcttg gtctcccta     6000 tagtgagtcg tattaatttc gataagccag taagcagtgg gttctctagt tagccagaga    6060 gcttttgca aaagcctagg cctccaaaaa agcctcctca ctacttctgg aatagctcag     6120
aggccgaggc ggcctcggcc tctgcataaa taaaaaaat tagtcagcca tggggcggag    6180
aatgggcgga actgggcgga gttaggggcg ggatgggcgg agttaggggc gggactatgg    6240
ttgctgacta attgagatgc atgctttgca tacttctgcc tgctggggag cctggggact    6300
ttccacaccc taactgacac acattccaca gccggatcga tgtgggccat cgccctgata    6360
gacggttttt cgccctttga cgttggagtc cacgttcttt aatagtggac tcttgttcca    6420
aactggaaca acactcaacc ctatctcggt ctattctttt gatttataag ggattttgcc    6480
gatttcggcc tattggttaa aaaatgagct gatttaacaa aaatttaacg cgaattaatt    6540
ctgtggaatg tgtgtcagtt agggtgtgga aagtccccag gctccccagc aggcagaagt    6600
atgcaaagca tgcatctcaa ttagtcagca accaggtgtg gaaagtcccc aggctcccca    6660
gcaggcagaa gtatgcaaag catgcatctc aattagtcag caaccatagt cccgccccta    6720
actccgccca tcccgcccct aactccgccc agttccgccc attctccgcc ccatggctga    6780 ctaattttt ttatttatgc agaggccgag gccgcctctg cctctgagct attccagaag    6840
tagtgaggag gcttttttgg aggcctaggc ttttgcaaaa agctcccggg agcttgtata    6900
tccattttcg gatctgatca agagacagga tgaggatcgt ttcgcatgat tgaacaagat    6960
ggattgcacg caggttctcc ggccgcttgg gtggagaggc tattcggcta tgactgggca    7020
caacagacaa tcggctgctc tgatgccgcc gtgttccggc tgtcagcgca ggggcgcccg    7080 gttcttttg tcaagaccga cctgtccggt gccctgaatg aactgcagga cgaggcagcg    7140
cggctatcgt ggctggccac gacgggcgtt ccttgcgcag ctgtgctcga cgttgtcact    7200
gaagcgggaa gggactggct gctattgggc gaagtgccgg ggcaggatct cctgtcatct    7260
caccttgctc ctgccgagaa agtatccatc atggctgatg caatgcggcg gctgcatacg    7320
cttgatccgg ctacctgccc attcgaccac caagcgaaac atcgcatcga gcgagcacgt    7380
actcggatgg aagccggtct tgtcgatcag gatgatctgg acgaagagca tcaggggctc    7440
gcgccagccg aactgttcgc caggctcaag gcgcgcatgc ccgacggcga gatctcgtc    7500 gtgacccatg gcgatgcctg cttgccgaat atcatggtgg aaaatggccg cttttctgga    7560
ttcatcgact gtggccggct gggtgtggcg gaccgctatc aggacatagc gttggctacc    7620
cgtgatattg ctgaagagct tggcggcgaa tgggctgacc gcttcctcgt gctttacggt    7680
atcgccgctc ccgattcgca gcgcatcgcc ttctatcgcc ttcttgacga gttcttctga    7740
```

```
gcgggactct ggggttcgaa atgaccgacc aagcgacgcc caacctgcca tcacgagatt   7800
tcgattccac cgccgccttc tatgaaaggt tgggcttcgg aatcgttttc cgggacgccg   7860
gctggatgat cctccagcgc ggggatctca tgctggagtt cttcgcccac cccaacttgt   7920
ttattgcagc ttataatggt tacaaataaa gcaatagcat cacaaatttc acaaataaag   7980 cattttttc actgcattct agttgtggtt tgtccaaact catcaatgta tcttatcatg   8040
tctgtatacc gtcgacctct agctagagct tggcgtaatc atggtcatag ctgtttcctg   8100
tgtgaaattg ttatccgctc acaattccac acaacatacg agccggaagc ataaagtgta   8160
aagcctgggg tgcctaatga gtgagctaac tcacattaat tgcgttgcgc tcactgcccg   8220
ctttccagtc gggaaacctg tcgtgccagc tgcattaatg aatcggccaa cgcgcgggga   8280
gaggcggttt gcgtattggg cgctcttccg cttcctcgct cactgactcg ctgcgctcgg   8340
tcgttcggct gcggcgagcg gtatcagctc actcaaaggc ggtaatacgg ttatccacag   8400
aatcagggga taacgcagga agaacatgt gagcaaaagg ccagcaaaag gccaggaacc   8460
gtaaaaaggc cgcgttgctg gcgtttttcc ataggctccg ccccctgac gagcatcaca   8520 aaaatcgacg ctcaagtcag aggtggcgaa acccgacagg actataaaga taccaggcgt   8580 ttcccctgg aagctccctc gtgcgctctc ctgttccgac cctgccgctt accggatacc   8640
tgtccgcctt tctcccttcg ggaagcgtgg cgctttctca tagctcacgc tgtaggtatc   8700
tcagttcggt gtaggtcgtt cgctccaagc tgggctgtgt gcacgaaccc cccgttcagc   8760
ccgaccgctg cgccttatcc ggtaactatc gtcttgagtc caacccggta agacacgact   8820
tatcgccact ggcagcagcc actggtaaca ggattagcag agcgaggtat gtaggcggtg   8880
ctacagagtt cttgaagtgg tggcctaact acggctacac tagaagaaca gtatttggta   8940
tctgcgctct gctgaagcca gttaccttcg gaaaaagagt tggtagctct tgatccggca   9000
aacaaaccac cgctggtagc ggttttttg tttgcaagca gcagattacg cgcagaaaaa   9060
aaggatctca agaagatcct ttgatctttt ctacggggtc tgacgctcag tggaacgaaa   9120
actcacgtta agggattttg gtcatgagat tatcaaaaag gatcttcacc tagatccttt   9180
taaattaaaa atgaagtttt aaatcaatct aaagtatata tgagtaaact tggtctgaca   9240
gttaccaatg cttaatcagt gaggcaccta tctcagcgat ctgtctattt cgttcatcca   9300
tagttgcctg actccccgtc gtgtagataa ctacgatacg ggagggctta ccatctggcc   9360
ccagtgctgc aatgataccg cgagacccac gctcaccggc tccagattta tcagcaataa   9420
accagccagc cggaagggcc gagcgcagaa gtggtcctgc aactttatcc gcctccatcc   9480
agtctattaa ttgttgccgg gaagctagag taagtagttc gccagttaat agtttgcgca   9540
acgttgttgc cattgctaca ggcatcgtgg tgtcacgctc gtcgtttggt atggcttcat   9600
tcagctccgg ttcccaacga tcaaggcgag ttacatgatc ccccatgttg tgcaaaaaag   9660
cggttagctc cttcggtcct ccgatcgttg tcagaagtaa gttggccgca gtgttatcac   9720
tcatggttat ggcagcactg cataattctc ttactgtcat gccatccgta agatgctttt   9780
ctgtgactgg tgagtactca accaagtcat tctgagaata gtgtatgcgg cgaccgagtt   9840
gctcttgccc ggcgtcaata cgggataata ccgcgccaca tagcagaact ttaaaagtgc   9900
tcatcattgg aaaacgttct tcgggcgaa aactctcaag gatcttaccg ctgttgagat   9960
ccagttcgat gtaacccact cgtgcaccca actgatcttc agcatctttt actttcacca   10020
gcgtttctgg gtgagcaaaa acaggaaggc aaaatgccgc aaaaaaggga ataagggcga   10080
cacggaaatg ttgaatactc atactcttcc tttttcaata ttattgaagc atttatcagg   10140
```

```
gttattgtct catgagcgga tacatatttg aatgtattta gaaaaataaa caaatagggg    10200
ttccgcgcac atttccccga aaagtgccac ctgacgtc                            10238

<210> SEQ ID NO 14
<211> LENGTH: 9683
<212> TYPE: DNA
<213> ORGANISM: Artificial Sequence
<220> FEATURE:
<223> OTHER INFORMATION: vector

<400> SEQUENCE: 14
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccactagt ccagtgtggt ggaattgccc     960
ttattcctca gtgacccagg agctgacaca cttagaaggg caattctgca gatcaccatg    1020
cagcgcgtga acatgatcat ggcagaatca ccaggcctca tcaccatctg ccttttagga    1080
tatctactca gtgctgaatg tacagttttt cttgatcatg aaaacgccaa caaaattctg    1140
aatcggccaa agaggtataa ttcaggtaaa ttggaagagt ttgttcaagg gaaccttgag    1200
agagaatgta tggaagaaaa gtgtagtttt gaagaagcac gagaagtttt tgaaaacact    1260
gaaagaacaa ctgaattttg gaagcagtat gttgatggag atcagtgtga gtccaatcca    1320
tgtttaaatg gcggcagttg caaggatgac attaattcct atgaatgttg gtgtccttt     1380 ggatttgaag gaaagaactg tgaattagat gtaacatgta acattaagaa tggcagatgc    1440
gagcagtttt gtaaaaatag tgctgataac aaggtggttt gctcctgtac tgagggatat    1500
cgacttgcag aaaaccagaa gtcctgtgaa ccagcagtgc catttccatg tggaagagtt    1560
tctgtttcac aaacttctaa gctcacccgt gctgagactg ttttcctga tgtggactat    1620 gtaaattcta ctgaagctga aaccattttg gataacatca ctcaaagcac ccaatcattt    1680
aatgacttca ctcgggttgt tggtggagaa gatgccaaac caggtcaatt cccttggcag    1740 gttgtttga atggtaaagt tgatgcattc tgtggaggct ctatcgttaa tgaaaaatgg    1800
attgtaactg ctgccactg tgttgaaact ggtgttaaaa ttacagttgt cgcaggtgaa    1860
cataatattg aggagacaga acatacagag caaaagcgaa atgtgattcg aattattcct    1920
caccacaact acaatgcagc tattaataag tacaaccatg acattgccct tctggaactg    1980
```

```
gacgaaccct tagtgctaaa cagctacgtt acacctattt gcattgctga caaggaatac    2040
acgaacatct tcctcaaatt tggatctggc tatgtaagtg gctggggaag ggtcttccac    2100
aaagggagat cagctttagt tcttcagtac cttagagttc cacttgttga ccgagccaca    2160
tgtcttcgat ctacaaagtt caccatctat aacaacatgt tctgtgctgg cttccatgaa    2220
ggaggtagag attcatgtca aggagatagt gggggacccc atgttactga agtggaaggg    2280
accagtttct taactggaat tattagctgg ggtgaagagt gtgcaatgaa aggcaaatat    2340
ggaatatata ccaaggtatc ccggtatgtc aactggatta aggaaaaaac aaagctcact    2400
taatgaaaga tggatttcca aggatccagc acagtggcgg ccgctcgagt ctagagggcc    2460
cgtttaaacc cgctgatcag cctcgactgt gccttctagt tgccagccat ctgttgtttg    2520
cccctccccc gtgccttcct tgaccctgga aggtgccact cccactgtcc tttcctaata    2580
aaatgaggaa attgcatcgc attgtctgag taggtgtcat tctattctgg ggggtggggt    2640
ggggcaggac agcaagggg aggattggga agacaatagc aggcatgctg gggatgcggt    2700
gggctctatg gcttctgagg cggaaagaac cagctggggc tctagggggt atccccacgc    2760
gccctgtagc ggcgcattaa gcgcggcggg tgtggtggtt acgcgcagcg tgaccgctac    2820
acttgccagc gccctagcgc ccgctccttt cgctttcttc ccttcctttc tcgccacgtt    2880
cgccggcttt ccccgtcaag ctctaaatcg ggggctccct ttagggttcc gatttagtgc    2940
tttacggcac cttcgacccc aaaaaacttg attagggctg tggaatgtgt gtcagttagg    3000
gtgtggaaag tccccaggct ccccagcagg cagaagtatg caaagcatgc atctcaatta    3060
gtcagcaacc aggtgtggaa agtccccagg ctccccagca ggcagaagta tgcaaagcat    3120
gcatctcaat tagtcagcaa ccatagtccc gcccctaact ccgcccatcc cgcccctaac    3180
tccgcccagt tccgcccatt ctccgcccca tggctgacta attttttttta tttatgcaga    3240 ggccgaggcc gcctcggcct ctgagctatt ccagaagtag tgaggaggct tttttggagg    3300
cctaggcttt tgcaaaaagc tctctggcta actagagaac ccactgctta ctggcttatc    3360
gaaattaata cgactcacta tagggagacc caagctggct agcgtttaaa cttaagcttg    3420
gtaccgagct cggatccact agtccagtgt ggtggaattg ccctttccgc agagcaatgg    3480
cggtgtctgc cgggtccgcg cggacctcgc ccagctcaga taaagtacag aaagacaagg    3540
ctgaactgat ctcagggccc aggcaggaca gccgaatagg gaaactcttg ggttttgagt    3600
ggacagattt gtccagttgg cggaggctgg tgaccctgct gaatcgacca acggaccctg    3660
caagcttagc tgtctttcgt tttcttttttg ggttcttgat ggtgctagac attccccagg    3720
agcgggggct cagctctctg gaccggaaat accttgatgg gctggatgtg tgccgcttcc    3780
ccttgctgga tgccctacgc ccactgccac ttgactggat gtatcttgtc tacaccatca    3840
tgtttctggg ggcactgggc atgatgctgg gcctgtgcta ccggataagc tgtgtgttat    3900
tcctgctgcc atactggtat gtgtttctcc tggacaagac atcatggaac aaccactcct    3960
atctgtatgg gttgttggcc tttcagctaa cattcatgga tgcaaaccac tactggtctg    4020
tggacggtct gctgaatgcc cataggagga atgcccacgt gccccttttgg aactatgcag    4080 tgctccgtgg ccagatcttc attgtgtact tcattgcggg tgtgaaaaag ctggatgcag    4140
actgggttga aggctattcc atggaatatt tgtcccggca ctggctcttc agtcccttca    4200
aactgctgtt gtcgaggag ctgactagcc tgctggtcgt gcactggggt gggctgctgc    4260
ttgacctctc agctggtttc ctgctctttt ttgatgtctc aagatccatt ggcctgttct    4320
ttgtgtccta cttccactgc atgaattccc agcttttcag cattggtatg ttctcctacg    4380
```

```
tcatgctggc cagcagccct ctcttctgct cccctgagtg gcctcggaag ctggtgtcct    4440 actgccccg aaggttgcaa caactgttgc ccctcaaggc agcccctcag cccagtgttt     4500
cctgtgtgta taagaggagc cggggcaaaa gtggccagaa gccagggctg cgccatcagc    4560
tgggagctgc cttcaccctg ctctacctcc tggagcagct attcctgccc tattctcatt    4620
ttctcaccca gggctataac aactggacaa atgggctgta tggctattcc tgggacatga    4680
tggtgcactc ccgctcccac cagcacgtga agatcaccta ccgtgatggc cgcactggcg    4740
aactgggcta ccttaaccct ggggtattta cacagagtcg gcgatggaag gatcatgcag    4800
acatgctgaa gcaatatgcc acttgcctga gccgcctgct tcccaagtat aatgtcactg    4860
agccccagat ctactttgat atttgggtct ccatcaatga ccgcttccag cagaggattt    4920
ttgaccctcg tgtggacatc gtgcaggccg cttggtcacc ctttcagcgc acatcctggg    4980
tgcaaccact cttgatggac ctgtctccct ggagggccaa gttacaggaa atcaagagca    5040
gcctagacaa ccacactgag gtggtcttca ttgcagattt ccctggactg cacttggaga    5100
attttgtgag tgaagacctg ggcaacacta gcatccagct gctgcagggg gaagtgactg    5160
tggagcttgt ggcagaacag aagaaccaga ctcttcgaga gggagaaaaa atgcagttgc    5220
ctgctggtga gtaccataag gtgtatacga catcacctag cccttcttgc tacatgtacg    5280
tctatgtcaa cactacagag cttgcactgg agcaagacct ggcatatctg caagaattaa    5340
aggaaaaggt ggagaatgga agtgaaacag gcctctacc cccagagctg cagcctctgt    5400
tggaagggga agtaaagggg ggccctgagc caacacctct ggttcagacc tttcttagac    5460
gccaacaaag gctccaggag attgaacgcc ggcgaaatac tcctttccat gagcgattct    5520
tccgcttctt gttgcgaaag ctctatgtct ttcgccgcag cttcctgatg acttgtatct    5580
cacttcgaaa tctgatatta ggccgtcctt ccctggagca gctggcccag gaggtgactt    5640
atgcaaactt gagacccttt gaggcagttg gagaactgaa tccctcaaac acggattctt    5700
cacattctaa tcctcctgag tcaaatcctg atcctgtcca ctcagagttc tgaaggggc    5760 cagatgttgg aagggcaatt cgagtctaga ggccccgccc tgatagacgg ttttcgccc    5820 tttgacgttg gagtccacgt tctttaatag tggactcttg ttccaaactg gaacaacact    5880
caaccctatc tcggtctatt cttttgattt ataagggatt ttgccgattt cggcctattg    5940
gttaaaaaat gagctgattt aacaaaaatt taacgcgaat taattctgtg gaatgtgtgt    6000
cagttagggt gtggaaagtc cccaggctcc ccagcaggca gaagtatgca aagcatgcat    6060
ctcaattagt cagcaaccag gtgtggaaag tccccaggct ccccagcagg cagaagtatg    6120
caaagcatgc atctcaatta gtcagcaacc atagtcccgc ccctaactcc gcccatcccg    6180
cccctaactc cgcccagttc cgcccattct ccgccccatg gctgactaat ttttttatt    6240 tatgcagagg ccgaggccgc ctctgcctct gagctattcc agaagtagtg aggaggcttt    6300
tttggaggcc taggcttttg caaaaagctc ccggagctt gtatatccat tttcggatct    6360
gatcaagaga caggatgagg atcgtttcgc atgattgaac aagatggatt gcacgcaggt    6420
tctccggccg cttgggtgga gaggctattc ggctatgact gggcacaaca gacaatcggc    6480
tgctctgatg ccgccgtgtt ccggctgtca gcgcaggggc gcccggttct ttttgtcaag    6540
accgacctgt ccggtgccct gaatgaactg caggacgagg cagcgcggct atcgtggctg    6600
gccacgacgg gcgttccttg cgcagctgtg ctcgacgttg tcactgaagc gggaagggac    6660
tggctgctat tgggcgaagt gccggggcag gatctcctgt catctcacct tgctcctgcc    6720
gagaaagtat ccatcatggc tgatgcaatg cggcggctgc atacgcttga tccggctacc    6780
```

```
tgcccattcg accaccaagc gaaacatcgc atcgagcgag cacgtactcg gatggaagcc    6840
ggtcttgtcg atcaggatga tctggacgaa gagcatcagg ggctcgcgcc agccgaactg    6900
ttcgccaggc tcaaggcgcg catgcccgac ggcgaggatc tcgtcgtgac ccatggcgat    6960
gcctgcttgc cgaatatcat ggtggaaaat ggccgctttt ctggattcat cgactgtggc    7020
cggctgggtg tggcggaccg ctatcaggac atagcgttgg ctacccgtga tattgctgaa    7080
gagcttggcg gcgaatgggc tgaccgcttc ctcgtgcttt acggtatcgc cgctcccgat    7140
tcgcagcgca tcgccttcta tcgccttctt gacgagttct tctgagcggg actctggggt    7200
tcgaaatgac cgaccaagcg acgcccaacc tgccatcacg agatttcgat tccaccgccg    7260
ccttctatga aaggttgggc ttcggaatcg ttttccggga cgccggctgg atgatcctcc    7320
agcgcgggga tctcatgctg gagttcttcg cccaccccaa cttgtttatt gcagcttata    7380
atggttacaa ataaagcaat agcatcacaa atttcacaaa taaagcattt ttttcactgc    7440
attctagttg tggtttgtcc aaactcatca atgtatctta tcatgtctgt ataccgtcga    7500
cctctagcta gagcttggcg taatcatggt catagctgtt tcctgtgtga aattgttatc    7560
cgctcacaat tccacacaac atacgagccg gaagcataaa gtgtaaagcc tggggtgcct    7620
aatgagtgag ctaactcaca ttaattgcgt tgcgctcact gcccgctttc cagtcgggaa    7680
acctgtcgtg ccagctgcat taatgaatcg gccaacgcgc ggggagaggc ggtttgcgta    7740
ttgggcgctc ttccgcttcc tcgctcactg actcgctgcg ctcggtcgtt cggctgcggc    7800
gagcggtatc agctcactca aaggcggtaa tacggttatc cacagaatca ggggataacg    7860
caggaaagaa catgtgagca aaaggccagc aaaaggccag gaaccgtaaa aaggccgcgt    7920
tgctggcgtt tttccatagg ctccgccccc ctgacgagca tcacaaaaat cgacgctcaa    7980
gtcagaggtg gcgaaacccg acaggactat aaagatacca ggcgtttccc cctggaagct    8040
ccctcgtgcg ctctcctgtt ccgaccctgc cgcttaccgg atacctgtcc gcctttctcc    8100
cttcgggaag cgtggcgctt tctcatagct cacgctgtag gtatctcagt tcggtgtagg    8160
tcgttcgctc caagctgggc tgtgtgcacg aaccccccgt tcagcccgac cgctgcgcct    8220
tatccggtaa ctatcgtctt gagtccaacc cggtaagaca cgacttatcg ccactggcag    8280
cagccactgg taacaggatt agcagagcga ggtatgtagg cggtgctaca gagttcttga    8340
agtggtggcc taactacggc tacactagaa gaacagtatt tggtatctgc gctctgctga    8400
agccagttac cttcggaaaa agagttggta gctcttgatc cggcaaacaa accaccgctg    8460
gtagcggttt ttttgtttgc aagcagcaga ttacgcgcag aaaaaaagga tctcaagaag    8520
atcctttgat cttttctacg gggtctgacg ctcagtggaa cgaaaactca cgttaaggga    8580
ttttggtcat gagattatca aaaaggatct tcacctagat ccttttaaat taaaaatgaa    8640
gttttaaatc aatctaaagt atatatgagt aaacttggtc tgacagttac caatgcttaa    8700
tcagtgaggc acctatctca gcgatctgtc tatttcgttc atccatagtt gcctgactcc    8760
ccgtcgtgta gataactacg atacgggagg gcttaccatc tggccccagt gctgcaatga    8820
taccgcgaga cccacgctca ccggctccag atttatcagc aataaaccag ccagccgaa    8880 gggccgagcg cagaagtggt cctgcaactt tatccgcctc catccagtct attaattgtt    8940
gccgggaagc tagagtaagt agttcgccag ttaatagttt cgcaacgtt gttgccattg    9000 ctacaggcat cgtggtgtca cgctcgtcgt ttggtatggc ttcattcagc tccggttccc    9060
aacgatcaag gcgagttaca tgatccccca tgttgtgcaa aaaagcggtt agctccttcg    9120
gtcctccgat cgttgtcaga agtaagttgg ccgcagtgtt atcactcatg gttatggcag    9180
```

```
cactgcataa ttctcttact gtcatgccat ccgtaagatg cttttctgtg actggtgagt    9240
actcaaccaa gtcattctga gaatagtgta tgcggcgacc gagttgctct tgcccggcgt    9300
caatacggga taataccgcg ccacatagca gaactttaaa agtgctcatc attggaaaac    9360
gttcttcggg gcgaaaactc tcaaggatct taccgctgtt gagatccagt tcgatgtaac    9420
ccactcgtgc acccaactga tcttcagcat cttttacttt caccagcgtt tctgggtgag    9480
caaaaacagg aaggcaaaat gccgcaaaaa agggaataag ggcgacacgg aaatgttgaa    9540
tactcatact cttcctttt caatattatt gaagcattta tcagggttat tgtctcatga    9600
gcggatacat atttgaatgt atttagaaaa ataaacaaat aggggttccg cgcacatttc    9660
cccgaaaagt gccacctgac gtc                                            9683

<210> SEQ ID NO 15
<211> LENGTH: 9781
<212> TYPE: DNA
<213> ORGANISM: Artificial Sequence
<220> FEATURE:
<223> OTHER INFORMATION: vector

<400> SEQUENCE: 15
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattgccc    960
ttattcctca gtgacccagg agctgacaca cttagaaggg caattctgca gataccatgc   1020
agcgcgtgaa catgatcatg gcagaatcac caggcctcat caccatctgc cttttaggat   1080
atctactcag tgctgaatgt acagtttttc ttgatcatga aaacgccaac aaaattctga   1140
atcggccaaa gaggtataat tcaggtaaat tggaagagtt tgttcaaggg aaccttgaga   1200
gagaatgtat ggaagaaaag tgtagttttg aagaagcacg agaagttttt gaaaacactg   1260
aaagaacaac tgaattttgg aagcagtatg ttgatggaga tcagtgtgag tccaatccat   1320
gtttaaatgg cggcagttgc aaggatgaca ttaattccta tgaatgttgg tgtcccttg    1380 gatttgaagg aaagaactgt gaattagatg taacatgtaa cattaagaat ggcagatgcg   1440
agcagttttg taaaaatagt gctgataaca aggtggtttg ctcctgtact gagggatatc   1500
gacttgcaga aaaccagaag tcctgtgaac cagcagtgcc atttccatgt ggaagagttt   1560
```

```
ctgtttcaca aacttctaag ctcacccgtg ctgagactgt ttttcctgat gtggactatg   1620
taaattctac tgaagctgaa accattttgg ataacatcac tcaaagcacc caatcattta   1680
atgacttcac tcgggttgtt ggtggagaag atgccaaacc aggtcaattc ccttggcagg   1740 ttgtttttgaa tggtaaagtt gatgcattct gtggaggctc tatcgttaat gaaaaatgga   1800
ttgtaactgc tgcccactgt gttgaaactg gtgttaaaat tacagttgtc gcaggtgaac   1860
ataatattga ggagacagaa catacagagc aaaagcgaaa tgtgattcga attattcctc   1920
accacaacta caatgcagct attaataagt acaaccatga cattgccctt ctggaactgg   1980
acgaacccct agtgctaaac agctacgtta cacctatttg cattgctgac aaggaataca   2040
cgaacatctt cctcaaattt ggatctggct atgtaagtgg ctggggaagg gtcttccaca   2100
aagggagatc agctttagtt cttcagtacc ttagagttcc acttgttgac cgagccacat   2160
gtcttcgatc tacaaagttc accatctata caacatgtt ctgtgctggc ttccatgaag   2220
gaggtagaga ttcatgtcaa ggagatagtg ggggaccccca tgttactgaa gtggaaggga   2280 ccagttttctt aactggaatt attagctggg gtgaagagtg tgcaatgaaa ggcaaatatg   2340
gaatatatac caaggtatcc cggtatgtca actggattaa ggaaaaaaca aagctcactt   2400
aatgaaagat ggatttccaa ggatccagca cagtggcggc cgctcggttc ctagagggcc   2460
cgtttaaacc cgctgatcag cctcgactgt gccttctagt tgccagccat ctgttgtttg   2520
cccctccccc gtgccttcct tgaccctgga aggtgccact cccactgtcc tttcctaata   2580
aaatgaggaa attgcatcgc attgtctgag taggtgtcat tctattctgg ggggtggggt   2640
ggggcaggac agcaagggg aggattggga agacaatagc aggcatgctg gggatgcggt   2700
gggctctatg gcttctgagg cggaaagaac cagctgggc tctagggggt atccccacgc   2760
gccctgtagc ggcgcattaa gcgcggcggg tgtggtggtt acgcgcagcg tgaccgctac   2820
acttgccagc gccctagcgc ccgctccttt cgctttcttc ccttcctttc tcgccacgtt   2880
cgccggcttt ccccgtcaag ctctaaatcg ggggctccct ttagggttcc gatttagtgc   2940
tttacggcac ctcgacccca aaaaacttga ttagggtgat ggttcacatc gatgcaattt   3000
cctcatttta ttaggaaagg acagtgggag tggcaccttc cagggtcaag gaaggcacgg   3060
gggaggggca acaacagat ggctggcaac tagaaggcac agtcgaggct gatcagcggg   3120
tttaaacggg ccctctagac tcgaattgcc cttccaacat ctggccccct tcagaactct   3180
gagtggacag gatcaggatt tgactcagga ggattagaat gtgaagaatc cgtgtttgag   3240
ggattcagtt ctccaactgc ctcaaagggt ctcaagtttg cataagtcac ctcctgggcc   3300
agctgctcca gggaaggacg gcctaatatc agatttcgaa gtgagataca agtcatcagg   3360
aagctgcggc gaaagacata gagctttcgc aacaagaagc ggaagaatcg ctcatggaaa   3420
ggagtatttc gccggcgttc aatctcctgg agcctttgtt ggcgtctaag aaaggtctga   3480
accagaggtg ttggctcagg gcccccttttt acttcccctt ccaacagagg ctgcagctct   3540
gggggtagag gccctgtttc acttccattc tccaccttttt cctttaattc ttgcagatat   3600
gccaggtctt gctccagtgc aagctctgta gtgttgacat agacgtacat gtagcaagaa   3660
gggctaggtg atgtcgtata caccttatgg tactcaccag caggcaactg cattttttct   3720
ccctctcgaa gagtctggtt cttctgttct gccacaagct ccacagtcac ttccccctgc   3780
agcagctgga tgctagtgtt gcccaggtct tcactcacaa aattctccaa gtgcagtcca   3840
gggaaatctg caatgaagac cacctcagtg tggttgtcta ggctgctctt gatttcctgt   3900
aacttggccc tccagggaga caggtccatc aagagtggtt gcacccagga tgtgcgctga   3960
```

```
aagggtgacc aagcggcctg cacgatgtcc acacgagggt caaaaatcct ctgctggaag    4020
cggtcattga tggagaccca aatatcaaag tagatctggg gctcagtgac attatacttg    4080
ggaagcaggc ggctcaggca agtggcatat tgcttcagca tgtctgcatg atccttccat    4140
cgccgactct gtgtaaatac cccagggtta aggtagccca gttcgccagt gcggccatca    4200
cggtaggtga tcttcacgtg ctggtgggag cgggagtgca ccatcatgtc ccaggaatag    4260
ccatacagcc catttgtcca gttgttatag ccctgggtga gaaaatgaga ataggggcagg    4320 aatagctgct ccaggaggta gagcagggtg aaggcagctc ccagctgatg gcgcagccct    4380
ggcttctggc cacttttgcc ccggctcctc ttatacacac aggaaacact gggctgaggg    4440
gctgccttga ggggcaacag ttgttgcaac cttcgggggc agtaggacac cagcttccga    4500
ggccactcag gggagcagaa gagagggctg ctggccagca tgacgtagga gaacatacca    4560
atgctgaaaa gctgggaatt catgcagtgg aagtaggaca caaagaacag gccaatggat    4620
cttgagacat caaaaagag caggaaacca gctgagaggg caagcagcag cccacccag     4680 tgcacgacca gcaggctagt cagctcctca gacaacagca gtttgaaggg actgaagagc    4740
cagtgccggg acaaatattc catggaatag ccttcaaccc agtctgcatc cagctttttc    4800
acacccgcaa tgaagtacac aatgaagatc tggccacgga gcactgcata gttccaaagg    4860
ggcacgtggg cattcctcct atgggcattc agcagaccgt ccacagacca gtagtggttt    4920
gcatccatga atgttagctg aaaggccaac aacccataca gataggagtg gttgttccat    4980
gatgtcttgt ccaggagaaa cacataccag tatggcagca ggaataacac acagcttatc    5040
cggtagcaca ggcccagcat catgcccagt gcccccagaa acatgatggt gtagacaaga    5100
tacatccagt caagtggcag tgggcgtagg gcatccagca aggggaagcg gcacacatcc    5160
agcccatcaa ggtatttccg gtccagagag ctgagccccc gctcctgggg aatgtctagc    5220
accatcaaga acccaaaaag aaaacgaaag acagctaagc ttgcagggtc cgttggtcga    5280
ttcagcaggg tcaccagcct ccgccaactg acaaatctg tccactcaaa acccaagagt     5340
ttccctattc ggctgtcctg cctgggccct gagatcagtt cagccttgtc tttctgtact    5400
ttatctgagc tgggcgaggt ccgcgcggac ccggcagaca ccgccattgc tctgcggaaa    5460
gggcaattcc accacactgg actagtggat ccgagctcgg taccaagctt aagtttaaac    5520
gctagccagc ttgggtctcc ctatagtgag tcgtattaat ttcgataagc cagtaagcag    5580
tgggttctct agttagccag agagcttttt gcaaaagcct aggcctccaa aaaagcctcc    5640
tcactacttc tggaatagct cagaggccga ggcggcctcg gcctctgcat aaataaaaaa    5700
aattagtcag ccatggggcg gagaatgggc ggaactgggc ggagttaggg gcgggatggg    5760
cggagttagg ggcgggacta tggttgctga ctaattgaga tgcatgcttt gcatacttct    5820
gcctgctggg gagcctgggg actttccaca ccctaactga cacacattcc acagccggat    5880
cgatgtgggc catcgccctg atagacggtt tttcgccctt tgacgttgga gtccacgttc    5940
tttaatagtg gactcttgtt ccaaactgga acaacactca accctatctc ggtctattct    6000
tttgatttat aagggatttt gccgatttcg gcctattggt taaaaaatga gctgatttaa    6060
caaaaattta acgcgaatta attctgtgga atgtgtgtca gttagggtgt ggaaagtccc    6120
caggctcccc agcaggcaga agtatgcaaa gcatgcatct caattagtca gcaaccaggt    6180
gtggaaagtc cccaggctcc ccagcaggca gaagtatgca aagcatgcat ctcaattagt    6240
cagcaaccat agtcccgccc ctaactccgc ccatcccgcc cctaactccg cccagttccg    6300
cccattctcc gccccatggc tgactaattt ttttatttta tgcagaggcc gaggccgcct    6360
```

```
ctgcctctga gctattccag aagtagtgag gaggcttttt tggaggccta ggcttttgca    6420
aaaagctccc gggagcttgt atatccattt tcggatctga tcaagagaca ggatgaggat    6480
cgtttcgcat gattgaacaa gatggattgc acgcaggttc tccggccgct tgggtggaga    6540
ggctattcgg ctatgactgg gcacaacaga caatcggctg ctctgatgcc gccgtgttcc    6600
ggctgtcagc gcaggggcgc ccggttcttt ttgtcaagac cgacctgtcc ggtgccctga    6660
atgaactgca ggacgaggca gcgcggctat cgtggctggc cacgacgggc gttccttgcg    6720
cagctgtgct cgacgttgtc actgaagcgg gaagggactg gctgctattg ggcgaagtgc    6780
cggggcagga tctcctgtca tctcaccttg ctcctgccga aaagtatcc atcatggctg     6840 atgcaatgcg gcggctgcat acgcttgatc cggctacctg cccattcgac caccaagcga    6900
aacatcgcat cgagcgagca cgtactcgga tggaagccgg tcttgtcgat caggatgatc    6960
tggacgaaga gcatcagggg ctcgcgccag ccgaactgtt cgccaggctc aaggcgcgca    7020
tgcccgacgg cgaggatctc gtcgtgaccc atggcgatgc ctgcttgccg aatatcatgg    7080
tggaaaatgg ccgcttttct ggattcatcg actgtggccg ctgggtgtg gcggaccgct     7140 atcaggacat agcgttggct acccgtgata ttgctgaaga cttggcggc gaatgggctg     7200 accgcttcct cgtgctttac ggtatcgccg ctcccgattc gcagcgcatc gccttctatc    7260
gccttcttga cgagttcttc tgagcgggac tctggggttc gaaatgaccg accaagcgac    7320
gcccaacctg ccatcacgag atttcgattc caccgccgcc ttctatgaaa ggttgggctt    7380
cggaatcgtt ttccgggacg ccggctggat gatcctccag cgcggggatc tcatgctgga    7440
gttcttcgcc caccccaact gtttattgc agcttataat ggttacaaat aaagcaatag     7500
catcacaaat ttcacaaata aagcattttt ttcactgcat tctagttgtg gtttgtccaa    7560
actcatcaat gtatcttatc atgtctgtat accgtcgacc tctagctaga gcttggcgta    7620
atcatggtca tagctgtttc ctgtgtgaaa ttgttatccg ctcacaattc cacacaacat    7680
acgagccgga agcataaagt gtaaagcctg gggtgcctaa tgagtgagct aactcacatt    7740
aattgcgttg cgctcactgc ccgctttcca gtcgggaaac ctgtcgtgcc agctgcatta    7800
atgaatcggc caacgcgcgg ggagaggcgg tttgcgtatt gggcgctctt ccgcttcctc    7860
gctcactgac tcgctgcgct cggtcgttcg gctgcggcga gcggtatcag ctcactcaaa    7920
ggcggtaata cggttatcca cagaatcagg ggataacgca ggaaagaaca tgtgagcaaa    7980
aggccagcaa aaggccagga accgtaaaaa ggccgcgttg ctggcgtttt tccataggct    8040
ccgcccccct gacgagcatc acaaaaatcg acgctcaagt cagaggtggc gaaacccgac    8100
aggactataa agataccagg cgtttccccc tggaagctcc ctcgtgcgct ctcctgttcc    8160
gaccctgccg cttaccggat acctgtccgc ctttctccct tcgggaagcg tggcgctttc    8220
tcatagctca cgctgtaggt atctcagttc ggtgtaggtc gttcgctcca agctgggctg    8280
tgtgcacgaa ccccccgttc agcccgaccg ctgcgcctta tccggtaact atcgtcttga    8340
gtccaacccg gtaagacacg acttatcgcc actggcagca gccactggta acaggattag    8400
cagagcgagg tatgtaggcg gtgctacaga gttcttgaag tggtggccta actacggcta    8460
cactagaaga acagtatttg gtatctgcgc tctgctgaag ccagttacct tcggaaaaag    8520
agttggtagc tcttgatccg gcaaacaaac caccgctggt agcggttttt tgtttgcaa    8580 gcagcagatt acgcgcagaa aaaaaggatc tcaagaagat cctttgatct tttctacggg    8640
gtctgacgct cagtggaacg aaaactcacg ttaagggatt ttggtcatga gattatcaaa    8700
aaggatcttc acctagatcc ttttaaatta aaaatgaagt tttaaatcaa tctaaagtat    8760
```

-continued

```
atatgagtaa acttggtctg acagttacca atgcttaatc agtgaggcac ctatctcagc    8820
gatctgtcta tttcgttcat ccatagttgc ctgactcccc gtcgtgtaga taactacgat    8880
acgggagggc ttaccatctg gccccagtgc tgcaatgata ccgcgagacc cacgctcacc    8940
ggctccagat ttatcagcaa taaaccagcc agccggaagg gccgagcgca gaagtggtcc    9000
tgcaacttta tccgcctcca tccagtctat taattgttgc cgggaagcta gagtaagtag    9060
ttcgccagtt aatagtttgc gcaacgttgt tgccattgct acaggcatcg tggtgtcacg    9120
ctcgtcgttt ggtatggctt cattcagctc cggttcccaa cgatcaaggc gagttacatg    9180
atcccccatg ttgtgcaaaa aagcggttag ctccttcggt cctccgatcg ttgtcagaag    9240
taagttggcc gcagtgttat cactcatggt tatggcagca ctgcataatt ctcttactgt    9300
catgccatcc gtaagatgct tttctgtgac tggtgagtac tcaaccaagt cattctgaga    9360
atagtgtatg cggcgaccga gttgctcttg cccggcgtca atacgggata ataccgcgcc    9420
acatagcaga actttaaaag tgctcatcat tggaaaacgt tcttcggggc gaaaactctc    9480
aaggatctta ccgctgttga gatccagttc gatgtaaccc actcgtgcac ccaactgatc    9540
ttcagcatct tttactttca ccagcgtttc tgggtgagca aaaacaggaa ggcaaaatgc    9600
cgcaaaaaag ggaataaggg cgacacggaa atgttgaata ctcatactct tcctttttca    9660
atattattga agcatttatc agggttattg tctcatgagc ggatacatat ttgaatgtat    9720
ttagaaaaat aaacaaatag gggttccgcg cacatttccc cgaaaagtgc cacctgacgt    9780
c                                                                   9781
```

COMPOSITIONS AND METHODS FOR PRODUCING GAMMA-CARBOXYLATED PROTEINS

CLAIM OF PRIORITY

This application is a continuation of U.S. patent application Ser. No. 10/964,888, filed Oct. 14, 2004, now issued as U.S. Pat. No. 7,842,477, which claims benefit of the foreign filing date of Great Britain Patent Application Serial No. 0324044.7, filed Oct. 14, 2003. The entire contents of each of these priority applications are considered part of the present application and are hereby incorporated in the present application in their entirety.

TECHNICAL FIELD

The present invention relates a host cell comprising an expression vector comprising a nucleic acid molecule encoding a protein requiring gamma-carboxylation and associated expression control sequences comprising a first promoter and a nucleic acid molecule encoding a γ-glutamyl carboxylase and associated expression control sequences comprising a second promoter. The invention further relates to a method of producing a protein requiring gamma-carboxylation in high yields.

BACKGROUND TO THE INVENTION

Bleeding is a common clinical problem. It is a consequence of disease, trauma, surgery and medicinal treatment. It is imperative to mechanically stop the bleeding. This may be difficult or even impossible due to the location of the bleeding or because it diffuses from many (small) vessels. Patients who are bleeding may thus require treatment with agents that support haemostasis. This may be blood-derived products (haemotherapy), agents that cause the release of endogenous haemostatic agents, recombinant coagulation factors (F), or agents that delay the dissolution of blood clots.

The first line treatment among the blood derived products, often obtained from the local hospital, are whole blood for volume substitution and support of haemostasis, packed red cells for the improvement of oxygen transporting capacity, platelet concentrates to raise the number of platelets (if low or defective) and fresh frozen plasma for support of the haemostasis (blood coagulation and platelet aggregation). Second line plasma derived products that support haemostasis are plasma cryoprecipitate, prothrombin complex concentrates, activated prothrombin complex concentrates and purified coagulation factors. Several coagulation factors are today available as human recombinant proteins, inactive (coagulation factors VIII and IX) and activated (coagulation factor VIIa).

Haemophilia is an inherited or acquired bleeding disorder with either abnormal or deficient coagulation factor or antibodies directed towards a coagulation factor which inhibits the procoagulant function. The most common haemophilias are haemophilia A (lack coagulation factor VIII) and haemophilia B (factor IX). The purified or recombinant single coagulation factors are the main treatment of patients with haemophilia. Patients with inhibitory antibodies posses a treatment problem as they may also neutralise the coagulation factor that is administered to the patient. The active form of Protein C (APC) is an inhibitor of plasma coagulation by degradation of the activated coagulation factors Va and VIIIa. Recombinant APC has been shown to be an effective treatment of undue plasma coagulation in patients with sepsis.

Coagulation factors for therapeutic use can be obtained from human plasma, although the purification process is not simple and requires many steps of which several aim at eliminating contaminating viruses. But even with extensive safety measures and testing of blood-derived products, contamination with infectious viruses or prions cannot be ruled out. Because of this risk it is highly desirable to produce human therapeutic proteins from recombinant cells grown in media without animal derived components. This is not always straightforward as many proteins require a mammalian host to be produced in a fully functional form, i.e. be correctly post-translationally modified. Among the coagulation factors commercially produced in recombinant cells are FVII (NovoSeven), FVIII (Kogenate, Recombinate, Refacto) and FIX (BeneFix) (Roddie and Ludlam. Blood Rev. 11:169-177, 1997) and Active Protein C (Xigris). One of the major obstacles in obtaining large amounts of fully functional recombinant human coagulation factors lies in the Gla-domain present in FII, FVII, FIX, FX and Protein C. This domain contains glutamic acid residues that are post-translationally modified by addition of carboxyl groups. The production of these factors are hampered by the fact that overexpression of them result in under-carboxylated, and hence inactive, protein. The Gla modifications are a result of the action of a vitamin K-dependent enzyme called γ-glutamyl carboxylase (GGCX). This enzyme has been extensively studied by many scientists, particularly those involved in coagulation factor research (WO-A-8803926; Wu et al. Science 254(5038):1634-1636, 1991; Rehemtulla et al., Proc Natl Acad Sci USA 90:46171-4615, 1993; Stanley J. Biol. Chem. 274(24):16940-16944, 1999; Vo et al., FEBS letters 445:256-260, 1999; Begley et al., The Journal of Biological Chemistry 275(46):36245-36249, 2000; Walker et al., The Journal of Biological Chemistry 276(11):7769-7774, 2001; Bandyopadhyay, et al. Proc Natl Acad Sci USA 99(3):1264-1269, 2002; Czerwiec et al., Eur J Biochem 269:6162-6172, 2002; Hallgren et al., Biochemistry 41(50):15045-15055, 2002; Harvey et al., The Journal of Biological Chemistry 278(10):8363-8369, 2003). Attempts to increase yields by co-expressing GGCX with coagulation factor FIX has been tried by at least two scientific groups but were not successful (Rehemtulla, et al. 1993, ibid; Hallgren et al. 2002, ibid). Considering the large interest in γ-carboxylated proteins, it may be assumed that many more co-expression trials have failed and thus have not been reported.

For human FII (prothrombin) at least 8 out of 10 Glu residues have to be correctly modified in order to obtain fully functional prothrombin (Malhotra, et al., J. Biol. Chem. 260: 279-287, 1985; Seegers and Walz 'Prothrombin and other vitamin K proteins', CRC Press, 1986). Extensive efforts to obtain high production levels of rhFII have been made using several different systems such as CHO cells, BHK cells, 293 cells and vaccinia virus expression systems, but have all failed or resulted in an under-carboxylated product and thus functionally inactive prothrombin (Jorgensen et al., J. Biol. Chem. 262:6729-6734, 1987; Russo et al., Biotechnol Appl Biochem 14(2):222-233, 1991; Fischer et al., J Biotechnol 38(2): 129-136, 1995; Herlitschka et al. Protein Expr. Purif. 8(3): 358-364, 1996; Russo et al., Protein Expr. Purif. 10:214-225, 1997; Vo et al. 1999, ibid; Wu and Suttie Thromb Res 96(2): 91-98, 1999). Earlier reported productivities for carboxylated recombinant human prothrombin are low; 20 mg/L for mutant prothrombin (Cote et al., J. Biol. Chem. 269:11374-11380, 1994), 0.55 mg/L for human prothrombin expressed in CHO cells (fully carboxylated, Jorgensen et al. 1987, ibid), 25 mg/L in CHO cells (degree of carboxylation not shown, Russo et al. 1997, ibid).

WO 92/19636 discloses the cloning and sequence identification of a human and bovine vitamin K dependent carboxylase. The application suggests co-expressing the vitamin K dependent carboxylase and a vitamin K dependent protein in a suitable host cell in order to prepare the vitamin K dependent protein. No co-expression of the carboxylase and vitamin K dependent protein is exemplified.

There is a need for improved methods to produce activated blood clotting factors in high yields. The present invention sets out to address this need.

SUMMARY OF THE INVENTION

According to a first aspect of the invention there is provided a host cell comprising an expression vector comprising a nucleic acid molecule encoding a protein requiring gamma-carboxylation and associated expression control sequences comprising a first promoter and a nucleic acid molecule encoding a γ-glutamyl carboxylase and associated expression control sequences comprising a second promoter, wherein the first promoter is sufficiently stronger than the second promoter so that the protein requiring gamma-carboxylation and the γ-glutamyl carboxylase are expressed in a ratio of at least 10:1.

According to another aspect of the invention there is provided a cell which is engineered to express (i) a protein which requires gamma-carboxylation, and (ii) a γ-glutamyl carboxylase, wherein the proteins (i) and (ii) are expressed in a ratio between 10:1 and 500:1.

According to another aspect of the invention there is provided genetically modified eukaryotic host cell comprising:
(i) a polynucleotide sequence encoding γ-glutamyl carboxylase protein wherein said γ-glutamyl carboxylase protein encoding sequence is operably linked to expression control sequences permitting expression of γ-glutamyl carboxylase protein by said cell; and
(ii) a polynucleotide encoding a protein requiring carboxylation by the γ-glutamyl carboxylase protein operably linked to expression control sequences permitting expression of said protein requiring carboxylation by said cell;
wherein the cell is capable of expressing the γ-glutamyl carboxylase protein and the protein requiring carboxylation in the ratio of at least 1:10.

According to a further aspect of the invention there is provided a vector comprising a nucleic acid molecule encoding a protein requiring gamma-carboxylation and associated expression control sequences comprising a first promoter and a nucleic acid molecule encoding a γ-glutamyl carboxylase and associated expression control sequences comprising a second promoter, wherein the first promoter is sufficiently stronger than the second promoter so that the protein requiring gamma-carboxylation and the γ-glutamyl carboxylase are expressed in a ratio of at least 10:1

According to yet another aspect of the invention there is provided a method for producing gamma-carboxylated protein comprising: (i) culturing a cell adapted to express a protein which requires gamma-carboxylation and γ-glutamyl carboxylase in a ratio of at least 10:1, under conditions suitable for expression of both proteins, and (ii) isolating gamma-protein. In one embodiment the method is used for producing gamma-carboxylated human Factor IX and in another embodiment the method is used for producing gamma-carboxylated human prothrombin. In another embodiment, the gamma-carboxylated protein produced is human gamma-carboxylated Factor X.

According to another aspect of the invention there is provided a method for production of a gamma-carboxylated protein in a mammalian cell line, comprising the step of co-expressing with said protein requiring gamma-carboxylation in the mammalian cell line a γ-glutamyl carboxylase, wherein the amount of expressed protein requiring gamma-carboxylation is at least 10-fold greater than the amount of expressed γ-glutamyl carboxylase, and (ii) isolating gamma-carboxylated protein. In one embodiment the method is used for producing gamma-carboxylated human Factor IX and in another embodiment the method is used for producing gamma-carboxylated human prothrombin. In another embodiment, the gamma-carboxylated protein produced is human gamma-carboxylated Factor X.

According to a further aspect of the invention there is provided isolated gamma-carboxylated protein produced according to the above methods, and the use of isolated gamma-carboxylated protein produced according to the above methods in coagulation therapy or the use of isolated gamma-carboxylated protein produced according to the above methods for the manufacture of a medicament for use in coagulation therapy. According to yet a further aspect of the invention there is provided a method of producing a pharmaceutical composition suitable for inducing blood clotting or promoting increased or decreased coagulation, comprising purifying active carboxylated protein expressed from a host cell adapted to express a protein requiring gamma-carboxylation and γ-glutamyl carboxylase in a ratio of between 10:1 and 500:1 and admixing the purified carboxylated protein with one or more pharmaceutically acceptable carriers or excipients and a pharmaceutical composition obtainable from the method. In one embodiment the active carboxylated protein is gamma-carboxylated human Factor IX and in another embodiment the active carboxylated protein is gamma-carboxylated human prothrombin. In another embodiment, the active carboxylated protein is gamma-carboxylated Factor X.

DETAILED DESCRIPTION OF THE INVENTION

Figure 1A:
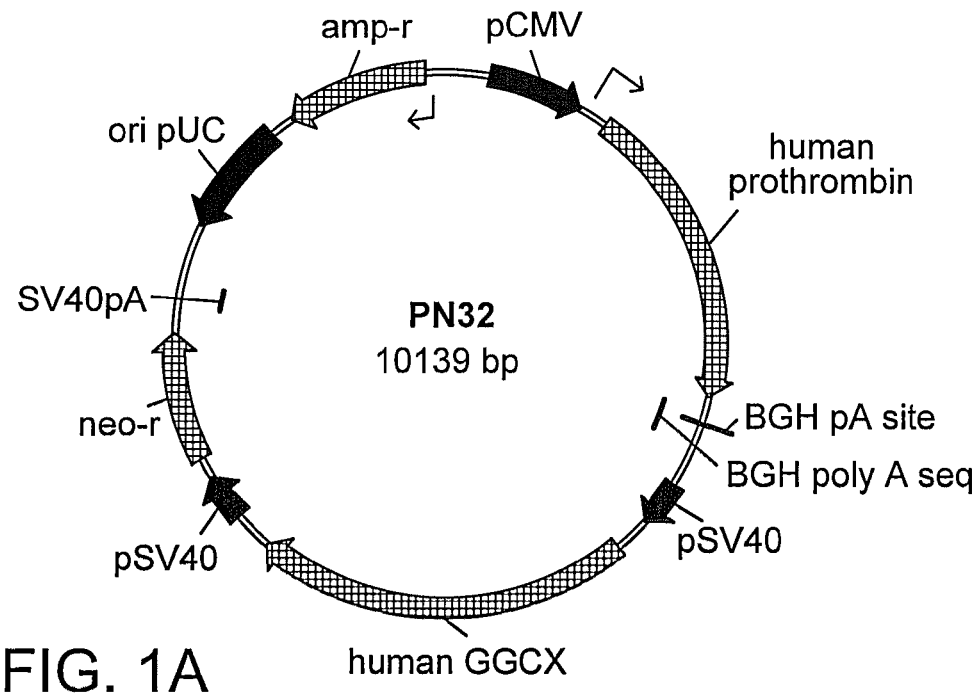
FIG. 1a illustrates a plasmid map of PN32 (prothrombin+GGCX) co-expression vector.

We have devised a different approach for expression of appropriately carboxylated recombinant vitamin K dependent coagulation factors at high levels, which involves co-expression of the vitamin K dependent coagulation factor and a γ-glutamyl carboxylase (GGCX) in a differential ratio. As one example we have expressed human prothrombin (rhFII) and human GGCX. Instead of using strong promoters for both rhFII and GGCX as others have tried (Rehemtulla et al., 1993, ibid; Hallgren et al., 2002, ibid), we used a strategy aiming at strong expression of FIT in combination with weak or very weak expression of the GGCX, such that the amount of expressed GGCX was less than $1/10^{th}$ of the expressed rhFII. To our surprise this strategy led to high levels of secreted correctly modified rhFII and good viability of the host cells, even when the cells were grown in animal component free chemically defined medium.

We have cloned GGCX and human prothrombin into an expression vector in such a way that the prothrombin mRNA level exceeds that of GGCX mRNA by a factor of at least 10. This results in production of a large excess of prothrombin protein compared to GGCX protein.

As a further example we have expressed rhFIX using the same GGCX co-expression vectors. This resulted in cell lines producing factor IX mRNA at levels exceeding GGCX mRNA levels by a factor of at least 10 in one case. In another cell line the factor IX: GGCX mRNA ratio was approximately 4-5:1. Only the cell line giving a ratio of at least 10:1 showed substantially increased rhFIX productivity (Table 1).

TABLE 1

Summary of productivity and carboxylated protein:GGCX mRNA ratio

| CLONE NAME/CONSTRUCT | PROTEIN PRODUCED | PRODUCTION* OF FULLY ACTIVE PROTEIN (mg/l) | CARBOXYLATED PROTEIN:GGCX, APPROX. mRNA RATIO | SOURCE OF DATA |
|---|---|---|---|---|
| P1E2/PN32 | Human prothrombin | 40 | 250:1 | Example 3 |
| B2F4/PP6 | | 26 | 50:1 | Example 5 |
| H3B10/PP6 | | 30 | 30:1 | Example 5 |
| E1A9/PText5 | | 3.5 | No GGCX | Example 3 |
| N4D5/F9NopA | Human FIX | 7.3 | 45:1 | Example 7 |
| P1G9/F9hglx | | 1.3 | 4:1 | Example 7 |
| IC4 | | 1¤ | No GGCX | Rehemtulla 1993, U.S. Pat. No. 5,460,950 |

*Productivity was measured from spinner cultures under similar growth conditions.
¤ Data from Rehemtulla 1993 and U.S. Pat. No. 5,460,950.

The vitamin K dependent coagulation factors (FII, FVII, FIX, FX and their activated forms FIIa or thrombin, FVIIa, FIXa, FXa) produced by the present method of co-expression with GGCX can be expected to be useful in the prevention and treatment of bleeding following trauma, surgery or diseases of the liver, kidneys, platelets or blood coagulation factors (haemophilia). Likewise the coagulation factor Protein C and its activated form APC can be expected to be useful in the prevention and treatment of disorders of increased coagulation with or without decreased levels of Protein C. The method is also applicable to other proteins that require post-translational carboxylation.

According to a first aspect of the invention there is provided a host cell comprising an expression vector comprising a nucleic acid molecule encoding a protein requiring gamma-carboxylation and associated expression control sequences comprising a first promoter and a nucleic acid molecule encoding a γ-glutamyl carboxylase and associated expression control sequences comprising a second promoter, wherein the first promoter is sufficiently stronger than the second promoter so that the protein requiring gamma-carboxylation and the γ-glutamyl carboxylase are expressed in a ratio of at least 10:1.

In a preferred embodiment the ratio of the expressed proteins is between 10:1 and 1000:1, more preferably between 10:1 and 500:1 and still more preferably between 25:1 and 250:1. A particularly suitable ratio is around 200:1.

In separate embodiments the ratio of the two expressed proteins can be at least 10:1, 30:1, 45:1, 50:1, 100:1, 200:1, 250:1, 300:1, 400:1, 500:1 and 1000:1.

In one particular embodiment, both the nucleic acid molecule encoding the protein requiring gamma-carboxylation and associated expression control sequences, and the nucleic acid molecule encoding the γ-glutamyl carboxylase and associated expression control sequences are located on the same expression vector. In another embodiment these two nucleic acid molecules are located on separate expression vectors.

According to a further aspect of the invention there is provided a nucleic acid according to SEQ ID NO: 14 and SEQ ID NO: 15.

According to a further aspect of the invention there is provided host cells transfected or transformed with a vector comprising the sequence of SEQ. ID NO: 14 or SEQ ID NO: 15 for the expression of human Factor IX.

According to a further aspect of the invention there is provided a host cell capable of expressing human coagulation factor IX and human gamma carboxylase enzymes, wherein the nucleic acid encoding the human coagulation factor IX and the nucleic acid encoding the gamma carboxylase are operably linked to control sequences that are capable of expressing the two proteins in a ratio of at least 10:1, respectively.

According to a further aspect of the invention there is provided a non-human eukaryotic host cell adapted to express human coagulation factor IX and human gamma carboxylase enzymes in a ratio of at least 10:1. In a particular embodiment, the nucleic acid encoding the human coagulation factor IX and the nucleic acid encoding the gamma carboxylase are operably linked to control sequences that are capable of expressing the two proteins in a ratio of at least 10:1, respectively.

According to a further aspect of the invention there is provided a host cell harbouring exogenous nucleic acid comprising human coagulation factor IX encoding nucleic acid under the control of hCMV promoter and human carboxylase encoding nucleic acid under the control of SV40 promoter.

According to a further aspect of the invention there is provided a nucleic acid according to SEQ. ID NO: 1, SEQ. ID NO: 2 or SEQ ID NO: 3.

According to a further aspect of the invention there is provided host cells transfected or transformed with a vector comprising the sequence of SEQ. ID NO: 1, SEQ. ID NO: 2 or SEQ ID NO: 3 for the expression of human prothrombin.

According to a further aspect of the invention there is provided host cells capable of expressing human prothrombin and human gamma carboxylase enzymes, wherein the nucleic acid encoding the human prothrombin and the nucleic acid encoding the gamma carboxylase are operably linked to control sequences that are capable of expressing the two proteins in a ratio of at least 10:1, respectively.

According to a further aspect of the invention there is provided a non-human eukaryotic host cell adapted to express human prothrombin and human gamma carboxylase enzymes in a ratio of at least 10:1. In a particular embodiment, the nucleic acid encoding the human prothrombin and the nucleic acid encoding the gamma carboxylase are operably linked to control sequences that are capable of expressing the two proteins in a ratio of at least 10:1, respectively.

According to a further aspect of the invention there is provided a host cell harbouring exogenous nucleic acid comprising human prothrombin encoding nucleic acid under the control of hCMV promoter and human carboxylase encoding nucleic acid under the control of SV40 promoter.

The invention has been exemplified using prothrombin and coagulation factor IX as the proteins requiring carboxylation. However, several proteins other than prothrombin and factor IX are dependent on correct γ-carboxylation for their full biological activity. Among those known from man are the coagulation factor FVII, which at present is only commercially produced in recombinant mammalian cells at relatively low levels (approximately 10 mg/L or less). The present invention will be applicable to improve the productivity of any protein that is dependent on γ-carboxylation, such proteins include, but are not limited to: prothrombin, coagulation factor II (FII), coagulation factor VII (FVII), coagulation factor IX (FIX); coagulation factor X (FX), Protein C, Protein S, Protein Z, Bone Gla protein (also known as: BGP or osteocalcin), Matrix Gla protein (MGP), proline rich Gla polypeptide 1 (PRRG1), proline rich Gla polypeptide 2 (PRRG2), Growth arrest-specific protein 6 (Gas 6). Other suitable proteins are: FXa-like protein in venom of elapid snake (subfamily Acanthophiina) and cone snail venom (*Conus textile*).

Each of these proteins, including their nucleic acid and amino acid sequences, are well known. Table 2 identifies representative sequences of wild-type and mutant forms of the various proteins that can be used in the present invention.

TABLE 2

| DESCRIPTION | CDNA EMBL ACC# | SPLICE VARIANTS (PROTEIN) | MUTATIONS | GENE EMBL ACC# |
|---|---|---|---|---|
| Glutamate gamma carboxylase | BC013979 | 2; BC013979; AF253530 | 1 SNP (EMBL# U65896); 2 SNPs (OMIM# 137167) | U65896 |
| Prothrombin | V00595 | 1; V00595 | approx. 100 SNP's (EMBL# AF478696) | AF478696 |
| Factor VII | AF466933 | 4; AF466933; AF272774; AR030786; AAN60063 | 21 SNPs (OMIM# 277500) | J02933 |
| Factor IX | A01819 | 3; A01819; A34669; M19063 | 5 SNPs (EMBL# AF536327); 108 SNPs (OMIM# 306900) | AF536327 |
| Factor X | BC046125 | 4; BC040125; M57285; AR095306; AB005892 | 118 SNPs (EMBL# AF503510); 14 SNPs (OMIM# 227600) | AF503510 |
| Protein C | BC034377 | 7; AB083690; AB083693; I09623; S50739; S72338 | 57 SNPs (EMBL# AF378903); 25 SNPs (OMIM# 176860) | AF378903 |
| Osteocalcin | AF141310 | 5; AF141310; AF141310; BC033656; X04143; X51699 | | X04143 |
| Matrix GLA protein | BC005272 | 1; BC005272 | | |
| Growth arrest-specific 6; AXL stimulatory factor | BC038984 | 1; BC038984 | | |
| Protein Z | M55670 | 2; AB033749; AB033749 | | |
| Proline-rich Gla (G-carboxyglutamic acid) polypeptide 1 | AF009242 | 2; AF009242; BC030786 | | |
| Proline-rich Gla (G-carboxyglutamic acid) polypeptide 2 | AF009243 | 2; AF009243; BC026032 | | |
| Vitamin K-dependent protein S precursor | BC015801 | 1; BC015801 | approx. 100 SNPs (EMBL# AY308744); 8 SNPs (OMIM# 176880) | AY308744 |

It will be appreciated that the invention is not restricted to a particular protein or protein encoding sequence of one of these proteins to be co-expressed. Moreover, and in particular with respect to blood coagulation factors, numerous mutant forms of the proteins have been disclosed in the art. The present invention is equally applicable to these mutant forms, including naturally occurring allelic variants, of the proteins as it is to wild-type sequence. In one embodiment the invention can be undertaking with any wild-type protein or one with at least 90%, preferably at least 95% sequence identity thereto.

The sequence identity between two sequences can be determined by pair-wise computer alignment analysis, using programs such as, BestFit, PILEUP, Gap or FrameAlign. The preferred alignment tool is BestFit. In practise, when searching for similar/identical sequences to the query search, from within a sequence database, it is generally necessary to perform an initial identification of similar sequences using suitable algorithms such as Blast, Blast2, NCBI Blast2, WashU Blast2, FastA, or Fasta3, and a scoring matrix such as Blosum 62. Such algorithms endeavour to closely approximate the "gold-standard" alignment algorithm of Smith-Waterman. Thus, the preferred software/search engine program for use in assessing similarity, i.e., how two primary polypeptide sequences line up is Smith-Waterman. Identity refers to direct matches, similarity allows for conservative substitutions.

The term "γ-glutamyl carboxylase" or "GGCX", as used herein, refers to a vitamin IC dependent enzyme that catalyses carboxylation of glutamic acid residues.

GGCX enzymes are widely distributed, and have been cloned from many different species such as the beluga whale *Delphinapterus leucas*, the toadfish *Opsanus tau*, chicken (*Gallus gallus*), hagfish (*Myxine glutinosa*), horseshoe crab (*Limulus polyphemus*), and the cone snail *Conus textile* (Begley et al., 2000, ibid; Bandyopadhyay et al. 2002, ibid). The carboxylase from conus snail is similar to bovine carboxylase and has been expressed in COS cells (Czerwiec et al. 2002, ibid). Additional proteins similar to GGCX can be found in insects and prokaryotes such as *Anopheles gambiae*, *Drosophila melanogaster* and *Leptospira* with NCBI accession numbers: gi 31217234, gi 21298685, gi 24216281, gi 24197548 and (Bandyopadhyay et al., 2002, ibid), respectively. The carboxylase enzyme displays remarkable evolutionary conservation. Several of the non-human enzymes have shown, or may be predicted to have, activity similar to that of the human GGCX we have used, and may therefore be used as an alternative to the human enzyme.

Table 3 identifies representative sequences of predicted proteins homologous to human GGXC (sorted after species origin) that can be used in the present invention.

TABLE 3

| Species | Data base accession #/ID |
| --- | --- |
| *Homo sapiens* (man) | NM_000821.2 |
|  | HUMGLUCARB |
|  | HUMHGCA |
|  | BC004422 |
|  | HSU65896 |
|  | AF253530.1 |
| *Papio hamadryas* (red baboon) | AC116665.1 |
| *Delphinapterus leucas* (white whale) | AF278713 |
| *Bos taurus* (bovine) | NM_174066.2 |
|  | BOVCARBOXG |
|  | BOVBGCA |
| *Ovis aries* (domestic sheep) | AF312035 |
| *Rattus norvegicus* (brown rat) | NM_031756.1 |
|  | AF065387 |
| *Mus musculus* (mouse) | NM_019802.1 |
|  | AF087938 |
| *Opsanus tau* (bony fishes) | AF278714.1 |
| *Conus textile* (molluscs) | AY0044904.1 |
|  | AF382823.2 |
| *Conus imperialis* (molluscs) | AF448234.1 |
| *Conus episcopatus* (molluscs) | AF448233.1 |
| *Conus omaria* (molluscs) | AF448235.1 |
| *Drosophila melanogaster* (fruit fly) | NM_079161.2 |
| *Anopheles gambiae* (mosquito) | XM_316389.1 |
| *Secale cereale* (monocots) | SCE314767 |
| *Triticum aestivum* (common wheat) | AF280606.1 |
| *Triticum urartu* (monocots) | AY245579.1 |
| *Hordeum vulgare* (barley) | BLYHORDCA |
| *Leptospira interrogans* (spirochetes) | AE011514.1 |
| *Streptomyces coelicolor* (high GC Gram+ bacteria) | SCO939109 |
|  | SCO939124 |
|  | AF425987.1 |
| *Streptomyces lividans* (high GC Gram+ bacteria) | SLU22894 |
| *Streptomyces viginiae* (high GC Gram+ bacteria) | SVSNBDE |
| *Micrococcus luteus* (high GC Gram+ bacteria) | MLSPCOPER |
| *Chlamydomonas reinhardtii* (green algae) | AF479588.1 |
| *Dictyostelium discoideum* (slime mold) | AC115612.2 |
| *Coturnix coturnix* (birds) | AF364329.1 |
| *Bradyrhizobium japonicum* (α-protoebacteria) | AP005937.1 |
| *Rhodobacter sphaeroides* (α-proteobacteria) | RSY14197 |
| *Sinorhizobium meliloti* (α-proteobacteria) | RME603647 |
|  | AF119834 |
| *Mesorhizobium loti* (α-proteobacteria) | AP003024.2 |
| *Chromobacterium violaceum* (β-proteobacteria) | AE016910.1 |
|  | AE016918.1 |
| *Pseudomonas aeruginosa* (γ-proteobacteria) | AE004613.1 |
|  | AF165882 |
| *Xanthomonas axonopodis* (γ-proteobacteria) | AE011706.1 |

TABLE 3-continued

| Species | Data base accession #/ID |
| --- | --- |
| Human herpesvirus 8 | KSU52064 |
|  | KSU75698 |
|  | AF305694 |
|  | AF360120 |
|  | AF192756 |

Each of the above-identified GGCX proteins and GGCX proteins from other species can be used as the carboxylase enzyme in the present invention.

One way to effect differential expression of the two co-expressed proteins is to use different promoters as part of the respective expression control sequences. The art is replete with examples of different promoters and other expression control sequences that are capable of expressing heterologous proteins to differing degrees or extents. Recombinant expression technology is suitably advanced such that a person skilled in the art of protein expression is able to select promoters and other control sequences to bring about co-expression of the protein requiring carboxylation and the carboxylase in the desired ratio. The selection of which particular promoters and other expression control sequences to use is a matter of individual choice.

In one embodiment, the control sequences associated with the protein requiring gamma-carboxylation comprise a strong promoter. In one embodiment this is the human cytomegalovirus (hCMV) immediate-early promoter. A strong promoter is here defined as a promoter giving rise to more than 1000 transcripts/cell. A weak promoter is here defined as a promoter giving rise to less than 1000 transcripts/cell.

In another embodiment, the control sequences associated with the γ-glutamyl carboxylase comprise a weak promoter. In one embodiment this is SV40 early promoter. In another embodiment the protein requiring gamma-carboxylation and the γ-glutamyl carboxylase are under the control of different promoter elements with the promoter controlling expression of the γ-glutamyl carboxylase being weaker that the promoter controlling expression of the protein requiring gamma-carboxylation.

In another embodiment, the γ-glutamyl carboxylase is under the control of SV40 early promoter and the protein requiring gamma-carboxylation is under the control of the human cytomegalovirus (hCMV) immediate-early promoter. In one embodiment according to this particular aspect of the invention the protein requiring gamma-carboxylation is human Factor X. In another embodiment the protein requiring gamma-carboxylation is human prothrombin. In another embodiment the protein requiring gamma-carboxylation is human Factor IX.

The invention has been exemplified by use of the strong CMV promoter (Boshart et al. Cell 41:521-530, 1985) to over-express Factor IX or prothrombin and the weaker SV40 promoter (Wenger et al. Anal Biochem 221:416-418, 1994) to control the GGCX expression. Other strong promoter that could be used according to the present invention include, but are not limited to, pEF-1α [human elongation factor-1α subunit gene) (Mizushima and Nagata, Nuc Acids Res 18:5322, 1990; Goldman et al., BioTechniques 21:1013-1015, 1996), pRSV [Rous sarcoma virus (Gorman et al., Proc Natl Acad Sci USA 79:6777-6781, 1982)] and pUbC [human ubiquitin (Schorpp et al., Nuc Acids Res 24:1787-1788, 1996)].

It is important to ensure that the protein to be produced (protein requiring carboxylation) is in excess compared to the modification enzyme, giving a ratio of at least 10:1. Ways to achieve a low level expression of the modification enzyme (γ-glutamyl carboxylase) include:

1) Use of a weak promoter to control expression of the modification enzyme including, but not limited to, SV40 immediate early promoter, the minimized FIX promoter (Rouet et al., The Journal of Biological Chemistry 267:20765-20773, 1992) or the HSV Thymidine kinase promoter (Wenger et al., 1994, ibid).

2) Mutate promoter or enhancer sequences of a strong promoter to reduce promoter strength.

3) Remove or change the Kozak sequence (translation initiation signal) to reduce the translation efficiency (Kozak. Nuc Acids Res 15:8125-8148, 1987; Kozak. Proc Natl Acad Sci USA 87:8301-83051987, 1990).

4) Clone nucleic acid encoding protein to be produced (protein requiring carboxylation) and nucleic acid encoding GGCX on separate vectors and transfect with a large excess of the construct containing the protein to be produced so as to generate a cell with multiple copies of the construct containing the protein to be produced 5) Clone DNA encoding protein to be produced and DNA encoding GGCX modification vectors on separate vectors, co-transfect or separately transfect, and use an amplification system to amplify the expression of the protein to be produced.

6) Isolate a stable cell line recombinantly expressing low levels of GGCX (but above endogenous levels) and use as host cell line for expression of proteins in need of γ-carboxylation.

7) Introduce mutation(s) into the GGCX in order to decrease GGCX substrate affinity.

In addition to these, the person skilled in the art of recombinant protein expression will be aware of other methods that could be used to generate a host cell that expresses the protein requiring carboxylation and the carboxylase protein in a ratio of at least 10:1.

According to a further aspect of the invention there is provided a cell which is engineered or adapted to express (i) a protein which requires gamma-carboxylation, and (ii) a γ-glutamyl carboxylase, wherein the proteins (i) and (ii) are expressed in a ratio between 10:1 and 500:1. In a particular embodiment the γ-glutamyl carboxylase is expressed between 2 and 5-fold above endogenous levels (i.e. that in a non-engineered or adapted cell).

According to a further aspect of the invention there is provided a recombinant cell adapted express (i) γ-glutamyl carboxylase protein above constitutive levels found in an equivalent unadapted cell and (ii) a protein requiring carboxylation, wherein the amount of expressed γ-glutamyl carboxylase protein and protein requiring carboxylation is in the ratio of at least 1:10.

According to a further aspect of the invention there is provided a genetically modified eukaryotic host cell comprising:

(i) a polynucleotide sequence encoding γ-glutamyl carboxylase protein wherein said γ-glutamyl carboxylase protein encoding sequence is operably linked to expression control sequences permitting expression of γ-glutamyl carboxylase protein by said cell; and (ii) a polynucleotide encoding a protein requiring carboxylation by the γ-glutamyl carboxylase protein operably linked to expression control sequences permitting expression of said protein requiring carboxylation by said cell;

wherein the cell is capable of expressing the γ-glutamyl carboxylase protein and the protein requiring carboxylation in the ratio of at least 1:10.

According to a further aspect of the invention there is provided a cell adapted to express a protein which requires gamma-carboxylation and γ-glutamyl carboxylase, wherein the nucleic acid encoding the protein which requires gamma-carboxylation and the nucleic acid encoding the γ-glutamyl carboxylase are under the control of regulatory sequences suitable for ensuring that the amount of expressed protein which requires gamma-carboxylation is at least 10-fold the amount of the γ-glutamyl carboxylase protein.

In one embodiment, at least one of the protein which requires gamma-carboxylation and the γ-glutamyl carboxylase is expressed from nucleic acid that has been introduced into the cell by recombinant technology. An alternate way of working the invention is to express endogenous protein (protein requiring carboxylation or carboxylase), but with substitution of the endogenous control sequences (promoter etc.) with heterologous sequences to effect the desired level of expression.

The host cell is preferably a eukaryotic cell. Typical host cells include, but are not limited to insect cells, yeast cells, and mammalian cells. Mammalian cells are particularly preferred. Suitable mammalian cells lines include, but are not limited to, CHO, HEK, NSO, 293, Per C.6, BHK and COS cells, and derivatives thereof. In one embodiment the host cell is the mammalian cell line CHO—S.

Overexpression of carboxylation dependent proteins has earlier generally resulted in undercarboxylated products. This is due to the endogenous host cell carboxylation capacity is being limited. On the other hand vast (16 to 70-fold) over expression of GGCX activity does not improve product yield (Rehemtulla et al., Proc Natl Acad Sci USA 90: 4611-4615, 1993), (Berkner and Pudota, Proc Natl Acad Sci USA. 95: 446-471, 1998), (Hallgren et al., Biochemistry 41(50): 15045-15055, 2002). The reason for this is not fully understood. Our invention requires a moderate over expression of GGCX. This ensures that greater than endogenous levels of GGCX are expressed from the cell, for example, where the GGCX activity level is elevated only 1.5 to 5-fold. At this moderately elevated level, surprisingly high levels of fully carboxylated rhFII were obtained as shown in Example 1.

It will therefore be appreciated that the expression ratio of the protein requiring carboxylation and the carboxylase that distinguishes this invention from previous co-expression teachings, excludes levels of GGCX that are endogenously produced. To meet the high productivity required it is necessary to express the carboxylase and the protein requiring carboxylation at levels above those found in normal cells.

In a preferred embodiment a cell or cell line is used which has little or no constitutively expressed carboxylase and/or protein requiring carboxylation.

In one embodiment the γ-glutamyl carboxylase is expressed at less than or equal to 10% of the amount of the protein which requires gamma-carboxylation. In alternate, further embodiments the γ-glutamyl carboxylase is expressed at less than or equal to 5%, 2%, 1%, 0.5%, 0.25% 0.1%, 0.05% or 0.01% of the amount of the protein which requires gamma-carboxylation.

The degree expression of the two proteins can be measured using techniques familiar to a person skilled in the art. These include direct measurements, for example measuring biological activity of the protein, or amount of protein (e.g. using antibodies), or indirect measurements, for example via measurement of mRNA transcript levels (e.g. Taqman analysis as in Example 3). The following references disclose ways of measuring GGCX enzyme activity (Lingenfelter et al., Biochemistry 35: 8234-8243, 1996; Berkner et al., Proc Natl Acad Sci USA 95: 446-471, 1998; Hallgren et al., Biochemistry 41(50): 15045-15055, 2002; and, Berkner et al., Proc Natl Acad Sci USA 89: 6242-6246, 1992).

For the purposes of this invention, the ratio of expression of the two proteins is determined indirectly via mRNA transcript level (e.g., by Taqman analysis).

In one embodiment the protein which requires gamma carboxylation is a vitamin K dependent coagulation factor. In a further embodiment, the protein which requires gamma-carboxylation is preferably selected from the group consisting of: prothrombin, coagulation factor II, coagulation FII, coagulation factor VII, coagulation FVII, coagulation factor IX, coagulation FIX, coagulation factor X, coagulation FX, Protein C, Protein S, Protein Z, Bone Gla protein, Matrix Gla protein, Growth arrest-specific protein 6 and Acanthophiinae FXa-like protein.

In one particular embodiment, the protein which requires gamma-carboxylation is Factor IX. In another particular embodiment, the protein which requires gamma-carboxylation is prothrombin. In another embodiment, the protein which requires gamma-carboxylation is Factor X.

The present invention has general application to proteins that require carboxylation from any source. However, if the expressed protein is to be used for human therapeutic purposes, human proteins are particularly preferred.

In one embodiment the γ-glutamyl carboxylase is of mouse, rat, bovine or conus snail origin. In another embodiment, the γ-glutamyl carboxylase is a human protein.

According to a further aspect of the invention there is provided a method for producing gamma-carboxylated protein comprising: (i) culturing a cell adapted to express a protein which requires gamma-carboxylation and γ-glutamyl carboxylase in a ratio of at least 10:1, under conditions suitable for expression of both proteins, and (ii) isolating gamma-carboxylated protein.

According to a further aspect of the invention there is provided a method for production of a gamma-carboxylated protein in a mammalian cell line, comprising the step of co-expressing with said protein requiring gamma-carboxylation in the mammalian cell line a γ-glutamyl carboxylase, wherein the amount of expressed protein requiring gamma-carboxylation is at least 10-fold greater than the amount of expressed γ-glutamyl carboxylase; and (ii) isolating gamma-carboxylated protein.

A method for producing a gamma-carboxylated protein comprising:
a) genetic modification of a eukaryotic cell to introduce a first polynucleotide encoding a protein that requires carboxylation and accompanying expression control sequences and a second polynucleotide encoding a γ-glutamyl carboxylase and accompanying expression control sequences to produce a eukaryotic host cell capable of co-expression of the protein that requires carboxylation and a γ-glutamyl carboxylase proteins in a ratio of at least 10:1';
b) cultivating the cell in suitable culture medium under conditions which allow the first and second polynucleotide sequences to be expressed; and c) isolation of the carboxylated protein from the medium or host cells.

Expression vectors usually include an origin of replication, a promoter, a translation initiation site, optionally a signal peptide, a polyadenylation site, and a transcription termination site. These vectors also usually contain one or more antibiotic resistance marker gene(s) for selection. Suitable expression vectors may be plasmids, cosmids or viruses such as phage or retroviruses. The coding sequence of the polypeptide is placed under the control of an appropriate promoter (i.e., HSV, CMV, TK, RSV, SV40 etc), control elements and transcription terminator (these are the associated expression control sequences) so that the nucleic acid sequence encoding the polypeptide is transcribed into RNA in the host cell transformed or transfected by the expression vector construct. The coding sequence may or may not contain a signal peptide or leader sequence for secretion of the polypeptide out of the host cell. Preferred vectors will usually comprise at least one multiple cloning site. In certain embodiments there will be a cloning site or multiple cloning site situated between the promoter and gene to be expressed. Such cloning sites can be used to create N-terminal fusion proteins by cloning a second nucleic acid sequence into the cloning site so that it is contiguous and in-frame with the gene sequence. In other embodiments there may be a cloning site or multiple cloning site situated immediately downstream of the gene to facilitate the creation of C-terminal fusions in a similar fashion to that for N-terminal fusions described above.

The host cell can be genetically modified (have extra nucleic acids introduced) by numerous methods, well known to a person skilled in the art, such as transfection, transformation and electroporation.

The invention also extends to purified gamma carboxylated protein produced by the methods of the present invention and their use in coagulant therapy.

According to yet another aspect of the invention there is provided a method of promoting increased or decreased coagulation in a subject comprising administering a pharmacologically effective amount of an isolated gamma-carboxylated protein obtained by the above-described methods to a patient in need thereof.

According to a further aspect of the invention there is provided a method of producing a pharmaceutical composition suitable for inducing blood clotting, comprising purifying active carboxylated protein expressed from a host cell adapted to express a protein requiring gamma-carboxylation and γ-glutamyl carboxylase in a ratio of at least 10:1 and admixing the purified carboxylated protein with one or more pharmaceutically acceptable carriers or excipients.

Protein-based therapeutics are usually stored frozen, refrigerated, at room temperature, and/or or in a freeze-dried state.

The compositions of the invention may be obtained by conventional procedures using conventional pharmaceutical excipients, well known in the art, but will most likely be in a form suitable for injection, either parenterally or directly into the wound site.

Aqueous suspensions generally contain the active ingredient in finely powdered form together with one or more suspending agents, such as sodium carboxymethylcellulose, methyl-cellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Powders suitable for preparation of an aqueous preparation for injection, by the addition of a suitable diluent, generally contain the active ingredient together with suitable carriers and excipients, suspending agent and one or more stabilisers or preservatives. The diluent may contain other suitable excipients, such as preservatives, tonicity modifiers and stabilizers.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate.

The pharmaceutical compositions of the invention may also be in the form of a sterile solution or suspension in a non-toxic parenterally acceptable diluent or solvent, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

For further information on Formulation the reader is referred to Chapter 25.2 in Volume 5 of Comprehensive Medicinal Chemistry (Corwin Hansch; Chairman of Editorial Board), Pergamon Press 1990; or, Volume 99 of Drugs and the pharmaceutical sciences; Protein formulation and delivery (Eugen J. McNally, executive editor), Marcel Dekker Inc 2000.

The amount of active ingredient that is combined with one or more excipients to produce a single dosage form will necessarily vary depending upon the host treated and the particular route of administration. For example, a formulation intended for injection to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of the active ingredient. Proteinaceous therapeutics are usually stored frozen or freeze-dried. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound will naturally vary according to the nature and severity of the conditions, the age and sex of the animal or patient and the route of administration, according to well known principles of medicine. In using a compound for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

The invention will be further described by the following non-limiting examples:

The practice of the present invention will employ, unless otherwise indicated, conventional methods of molecular biology and recombinant DNA techniques within the skill of the art. Such techniques are explained fully in the literature. See, e.g., Sambrook et al., eds., Molecular Cloning: A Laboratory Manual (3$^{rd}$ ed.) Cold Spring Harbor Laboratory Press, Cold Spring Harbor, N.Y. (2001); Ausubel et al., eds., Current Protocols in Molecular Biology, John Wiley & Sons, New York, N.Y. (2002); Glover & Hames, eds., DNA Cloning 3: A Practical Approach, Vols. I, II, & III, IRL Press, Oxford (1995); Colowick & Kaplan, eds., Methods in Enzymology, Academic Press; Weir at al., eds., Handbook of Experimental Immunology, 5$^{th}$ ed., Blackwell Scientific Publications, Ltd., Edinburgh, (1997).

EXAMPLE 1

Amplification of cDNA Encoding Human FII (hPT) and Human GGCX

Human liver mRNA was purchased from Clontech and cDNA synthesis was performed using the Superscript system from Invitrogen. The obtained cDNA was used as template for amplification of human FII using:

```
primer PTF0
                                              (SEQ ID NO: 3)
5'-ATTCCTCAGTGACCCAGGAGCTGACA-3',
and primer PTEXT
                                              (SEQ ID NO: 4)
5'-CTACTCTCCAAACTGATCAATGACCTTCTGTATCCACTTCTT-3',.
```

Human GGCX was amplified using

```
                                              (SEQ ID NO: 5)
   primer hglx5,   5'-TCCGCAGAGCAATGGCGGTGTCT-3',
   and (SEQ ID NO: 6)
   hglx3,          5'-CCAACATCTGGCCCCTTCAGAACT-3',.
```

Figure 1B:
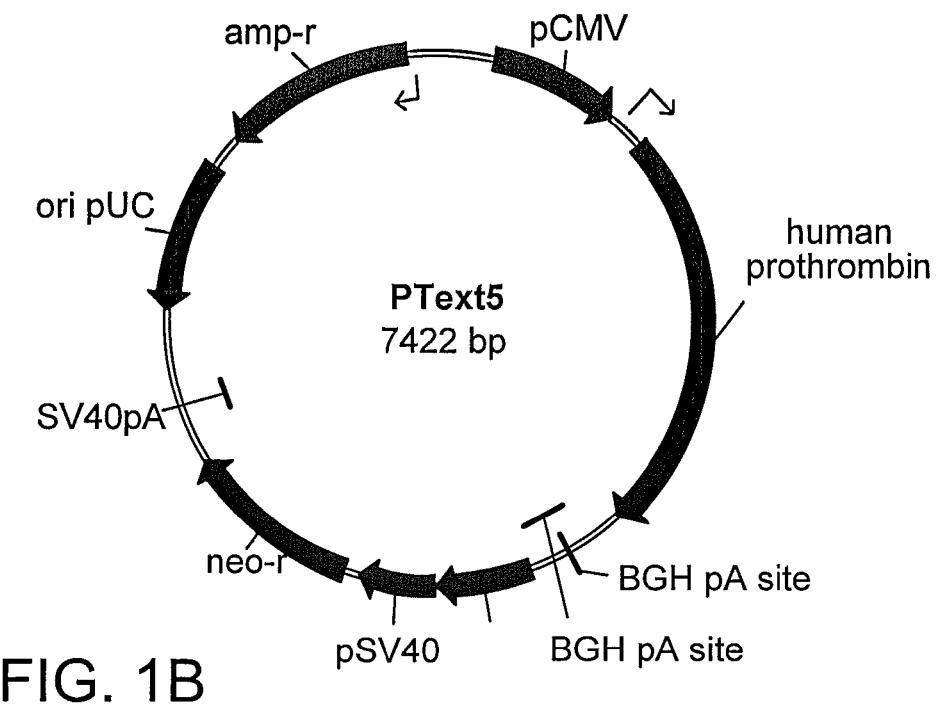
FIG. 1b represents a plasmid map of Ptext5 (prothrombin) expression vector.

The FII-encoding PCR product was cloned directly into the TA-TOPO treated vector pCDNA3.1V5/His (Invitrogen). Selection of a clone with hFII cDNA inserted in the correct direction gave the Ptext5 control construct (FIG. 1b). GGCX encoding cDNA under the control of the SV40 promoter was obtained by transfer of the GGCX encoding fragment from pCDNA3.1V5/His TA-TOPO to the pZeoSV2+ vector (Invitrogen), using restriction enzymes BamHI and NotI. The EcoRV-NotI restriction sites downstream of the GGCX insert were removed. A blunted ClaI-BclI fragment from the resulting paoSV2-GGCX plasmid (containing the SV40 promoter and the GGCX containing insert, but not the polyadenylation site and polyadenylation signal downstream of the GGCX encoding sequence) was then cloned into the blunted DraIII restriction site of pCDNA3.1+ (Invitrogen). A clone with the pSV40-GGCX fragment inserted in tandem (same transcriptional direction) relative to the CMV promoter was selected and a blunted KpnI-NotI F11 encoding fragment from Ptext5 was cloned into the EcoRV site to obtain the PN32 construct (FIG. 1a). The DNA sequences of PN32 and Ptext5 are as in Appendix 2. All cloning methods were according to standard methods and/or manufacturers' recommended procedures.

The PN32 construct contains the following key features:
Human cytomegalovirus (hCMV) immediate-early promoter controlling transcription of human prothrombin cDNA followed by the Bovine Growth Hormone (BGH) polyadenylation signal for efficient transcription termination and polyadenylation of mRNA.
SV40 early promoter controlling transcription of human γ-carboxylase cDNA (GGCX) without apparent polyadenylation site or signal.
Other features are as shown in FIG. 1 a).
For comparison the PText5 construct without GGCX was used (FIG. 1b). PTEXT5 nucleotide sequence is shown in SEQ ID NO: 1. PN32 nucleotide sequence is shown in SEQ ID NO: 2

Prothrombin Producing Cell Lines Obtained

The two constructs in FIG. 1 were transfected into CHO-S cells (Invitrogen). Stable transfectants were selected and screened for highly productive clones using a commercially available assay for prothrombin activity (Chromogenix). In this assay the prothrombin containing samples were first treated with snake venom toxin (Ecarin—available from Sigma) to generate thrombin. Thrombin activity was then assayed by addition of a chromogenic substrate (S-2238)—which generates colour when processed by thrombin. Transfection and selection of clones were done in parallel with both constructs. Cell culturing was done in DMEM medium containing 9% heat inactivated fetal bovine serum. Clones obtained were then adapted to growth in animal component free medium. The best producing clone obtained was from transfection with PN32 (FII+ GGCX), which yielded up to 400 mg/L human recombinant prothrombin when grown in animal component free chemically defined medium (far in excess of any published levels). Recombinantly produced rhFII was purified (according to the method disclosed in Josic et al., Journal of Chromatography B, 790:183497, 2003), and fractionated by ion-exchange chromatography using a Q-Sepharose column according to standard techniques, to obtain pure fully-carboxylated rhFII. Of fermentor produced rhFII up to 78 mg/L was fully-carboxylated and had the same biological activity as prothrombin purified from human plasma. Carboxylation was analysed by N-terminal sequencing of the protein and by prothrombinase assay (Mao et al. JBC, 273:30086-30091, 1998). Thrombin generation was triggered in human platelet-poor plasma by the addition of tissue factor, and the endogenous thrombin potential was measured essentially as described by Stig et al., (Blood Coagulation and Fibrinolysis, 14:457-462, 2003).

The best clone obtained with the PText5 construct gave a productivity of up to 10 mg/L in animal component free chemically defined medium, which is in the same range reported in the literature. The share of fully-carboxylated prothrombin obtained from the PText5 clone was estimated at around 50%. The final recovery of fully active rhFII was thus at least ten times higher using the PN32 construct containing a low expression level arrangement of the γ-carboxylase. For each of the constructs several clones with similar expression levels were identified.

EXAMPLE 2

Measurement of Ggcx Activity in Cho Cell Lines

Two rhFII producing CHO-S cell lines, obtained by transfection with the PN32 construct (co-expression of human GGCX) and PTEXT5 (no co-expression of GGCX), respectively, were grown in spinner bottles using protein free medium supplemented with 5 µg/ml vitamin K. One tenth of the growth medium was replaced daily. Cells were harvested after 7 days of culture and microsomes were prepared as described by Berkner et al., (Proc Natl Acad Sci USA 89: 6242-6246 1992). Human recombinant FII was purified from the culture supernate of the harvested cells. GGCX activity was measured as described by Berkner and Pudota (Proc Natl Acad Sci USA 95: 446-471 1998; and, Lingenfelter and Berkner (Biochemistry 35: 8234-8243, 1996). Our measurements showed that the GGCX activity is 1.5 times higher in the human GGCX co-expressing CHO cell line compared to the CHO cell line expressing only rhFII, using the same growth conditions.

EXAMPLE 3

Real Time Reverse Transcription Polymerase Chain Reaction (RT-PCR) analysis of mRNA Expression of γ-Carboxylase and Prothrombin in CHO-S Cell Lines Two CHO-S cell lines obtained by stable transfection with the PN32 (FII+GGCX) and Ptext5 (only FII) constructs respectively, were cultured in spinner bottles using protein free medium supplemented with vitamin K. Culture samples were withdrawn after 4, 5 and 6 days of culture to cover the estimated peak levels in mRNA production. RNA was isolated with Trizol™ according to the protocol supplied by the vendor, Invitrogen. The isolated RNA was DNaseI treated with the kit DNA-free™ from Ambion. cDNA synthesis was carried out using random hexamer primers and kit contents from Superscript™First-Strand Synthesis System for RT-PCR, Invitrogen.

Primers and Vic-labeled probes for Real-Time RT-PCR were selected using the software Primer Express™, Applied Biosystems.

Human γ-Carboxylase Oligonucleotides

```
                                          (SEQ ID NO: 7)
5'ACACCTCTGGTTCAGACCTTTCTT 3'  Forward primer (SEQ ID NO: 8)
5'AATCGCTCATGGAAAGGAGTATTT 3'  Reverse primer (SEQ ID NO: 9)
5'CAACAAAGGCTCCAGGAGATTGAACGC 3'  Probe
```

Amplicon length 86 bp
Human Prothrombin Oligonucleotides

```
                                          (SEQ ID NO: 10)
5' TGGAGGACAAAACCGAAAGAGA 3'  Forward primer (SEQ ID NO: 11)
5' CATCCGAGCCCTCCACAA 3'       Reverse primer (SEQ ID NO: 12)
5' CTCCTGGAATCCTACATCGACGGGC 3'  Probe
```

Amplicon length 69 bp

Primers were manufactured by Operon/Qiagen and the probes were ordered from Applied Biosystems. Rodent GAPDH control primers and probe were also used (Applied Biosystems; ABI #4308318 TaqMan® Rodent GAPDH Control Reagents Protocol)-Amplicon length 177 bp. The Real-Time RT-PCR reactions were performed on the ABI Prism™ 7700 Sequence detector, Applied Biosystems. The expected length of the amplified PCR products was confirmed on agarose gels. Dilution series to investigate the efficiency of the PCR reactions were carried out for all three genes. Expression levels of γ-Carboxylase and Prothrombin are presented relative to the expression of the control gene, rodent GAPDH.

Prothrombin

|  | CHO-S PText5 day 4 | CHO-S PText5 day 5 | CHO-S PText5 day6 | CHO-S PN32 day 4 | CHO-S PN32 day 5 | CHO-S PN32 day 6 |
|---|---|---|---|---|---|---|
| 2^-delta Ct | 0.008014 | 0.076239 | 0.066677 | 0.204948 | 0.322343 | 0.364334 |

γ-Carboxylase

|  | CHO-S PText5 day 4 | CHO-S PText5 day 5 | CHO-S PText5 day 6 | CHO-S PN32 day 4 | CHO-S PN32 day 5 | CHO-S PN32 day 6 |
|---|---|---|---|---|---|---|
| 2^-delta Ct | 3.39E−07 | 0 | 0 | 0.000277 | 0.00159 | 0.001568 |

From the relative expression levels the of rhFII:GGCX detected, ratios of approximately 74-232:1 were calculated depending on day of sample collection. For the cell line transfected with PN32, co-expression rhFII and GGCX, the number of transcript per cell were calculated to be approximately 8 for the GGCX mRNA and approximately 2000 for the rhFII mRNA, thus giving a rhFIIGGCX ratio of approximately 250:1. The GAPDH control mRNA transcripts/cell was for the same sample approximately 4000.

EXAMPLE 4

Production of Human FII

Figure 2:
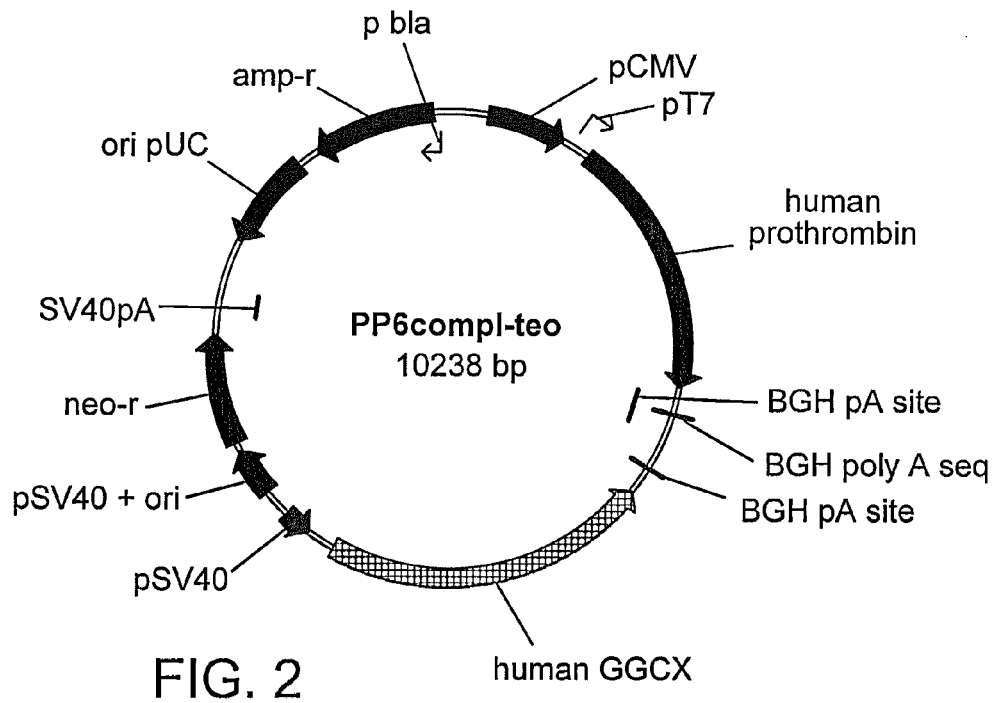
FIG. 2 represents a plasmid map of PP6 (prothrombin+GGCX) co-expression vector.

The human FII and GGCX cDNA cloned in Example 1 were inserted into pCDNA3.1 similarly as in Ex. 1. In order to give higher GGCX levels, the polyadenylation signal from pZeoSV2+ was included in the pSV40-GGCX-pA fragment cloned into the blunted DraIII site of pCDNA3.1. A clone with the GGCX-containing fragment in the reverse order compared to Ex. 1 was selected. Cloning of the F11 fragment was then done the same way as in Ex 1. The final construct PP6 is shown in FIG. 2 and the PP6 nucleotide sequence is shown in SEQ ID NO: 13.

Two prothrombin producing cell lines, B2F4 and H3B10 were obtained by transfecting CHO-S as described in Ex 1. Prothrombin from these two cell lines was purified and characterized as in Ex 1. Cultures of B2F4, gave productivities ranging from 30-70 mg/L and the share of fully carboxylated from 55-87% (the more rhFII the less fully carboxylated). Addition of butyrate gave a somewhat higher productivity but decreased the share of fully carboxylated rhFII and was not considered to be beneficial. H3B10 is slow-growing and gave a productivity of about 50 mg/L, which was high relative to the amount of cells in the culture, and the share of fully carboxylated rhFII was around 60%. Compared to the cell line obtained in example 1, less fully carboxylated rhFII was produced using the PP6 construct for a CHO cell line. The production of fully active recombinant prothrombin is still, however, far above earlier published levels.

EXAMPLE 5

Real Time RT-PCR analyses of the expression of γ-Carboxylase and Prothrombin in CHO-S Cell Lines by Measuring Amount of mRNA The B2F4 and H3B10 cell lines from example 4 were analysed by real-time PCR analyses by the same method and the same primers as in Ex 3. Culture samples of 10 ml were collected at peak productivity in order to be equivalent to samples in Ex 3. For clone H3B10 samples were from day 10 due to the slow growth of this clone, and for clone B2F4 samples were from day 6.

TABLE 4

Results from Real time RT-PCR analyses of prothrombin producing cell lines co-expressing GGCX.

| Transcript | Total # cells | Resulting amount of total RNA | Total RNA used for RT-PCR | Amount mRNA in RT-PCR | Number of cells in RT-PCR | Ct | Copies mRNA | Copies mRNA/cell |
|---|---|---|---|---|---|---|---|---|
| P1E2 * Day 6 |  |  |  |  |  |  |  |  |
| PT | 2.00E+07 | 2.39E−04 | 1.25E−08 | 2.50E−09 | 1.05E+03 | 19 | 2.10E+06 | 2005 |
| GGCX | 2.00E+07 | 2.39E−04 | 1.25E−08 | 2.50E−09 | 1.05E+03 | 27 | 8.19E+03 | 8 |
| GAPDH | 2.00E+07 | 2.39E−04 | 1.25E−08 | 2.50E−09 | 1.05E+03 | 18 | 4.19E+06 | 4010 |
| B2F4-1 Day 6 |  |  |  |  |  |  |  |  |
| PT | 1.30E+07 | 2.20E−04 | 1.25E−08 | 2.50E−09 | 7.39E+02 | 19.2 | 1.83E+06 | 2472 |
| GGCX | 1.30E+07 | 2.20E−04 | 1.25E−08 | 2.50E−09 | 7.39E+02 | 24.1 | 6.11E+04 | 83 |

TABLE 4-continued

Results from Real time RT-PCR analyses of prothrombin producing cell lines co-expressing GGCX.

| Transcript | Total # cells | Resulting amount of total RNA | Total RNA used for RT-PCR | Amount mRNA in RT-PCR | Number of cells in RT-PCR | Ct | Copies mRNA | Copies mRNA/cell |
|---|---|---|---|---|---|---|---|---|
| GAPDH B2F4-2 Day 6 | 1.30E+07 | 2.20E−04 | 1.25E−08 | 2.50E−09 | 7.39E+02 | 19.8 | 1.20E+06 | 1631 |
| | | | | | | | | |
| PT | 1.10E+07 | 1.40E−04 | 1.25E−08 | 2.50E−09 | 9.82E+02 | 19.2 | 1.83E+06 | 1859 |
| GGCX | 1.10E+07 | 1.40E−04 | 1.25E−08 | 2.50E−09 | 9.82E+02 | 24.1 | 6.11E+04 | 62 |
| GAPDH H3B10-1 Day 10 | 1.10E+07 | 1.40E−04 | 1.25E−08 | 2.50E−09 | 9.82E402 | 19 | 2.10E+06 | 2135 |
| | | | | | | | | |
| PT | 1.10E+07 | 2.90E−04 | 1.25E−08 | 2.50E−09 | 4.74E+02 | 17.77 | 4.92E+06 | 10375 |
| GGCX | 1.10E+07 | 2.90E−04 | 1.25E−08 | 2.50E−09 | 4.74E+02 | 23.4 | 9.93E+04 | 210 |
| GAPDH H3B10-2 Day 10 | 1.10E+07 | 2.90E−04 | 1.25E−08 | 2.50E−09 | 4.74E+02 | 17.96 | 4.31E+06 | 9095 |
| | | | | | | | | |
| PT | 8.90E+06 | 3.10E−04 | 1.25E−08 | 2.50E−09 | 3.59E+02 | 19.2 | 1.83E+06 | 5087 |
| GGCX | 8.90E+06 | 3.10E−04 | 1.25E−08 | 2.50E−09 | 3.59E+02 | 25.3 | 2.66E+04 | 74 |
| GAPDH | 8.90E+06 | 3.10E−04 | 1.25E−08 | 2.50E−09 | 3.59E+02 | 18.9 | 2.25E+06 | 6263 |

Two independent 100 ml spinner cultures for each B2F4 and H3B10 were sampled for Real-Time RT-PCR analyses.
* P1E2 data from example 3 for comparison.

The calculated ratio rhFII mRNA: GGCX mRNA was approximately 30:1 for clone H3B10, approximately 50:1 for clone B2F4 and approximately 250:1 for clone P1E2.

EXAMPLE 6

Production of Human Coagulation Factor IX (FIX)

Human coagulation factor IX cDNA was amplified from human Gene pool liver cDNA purchased from Invitrogen. Oligonucleotide primers were for

```
the 5'-end; F9f.ampl.:
5'-CACCATGCAGCGCGTGAACATGAT-3',    (SEQ ID NO: 16)

and the 3'-end; F9r.ampl.:
5'-CCTTGGAAATCCATCTTTCATTA-3'.     (SEQ ID NO: 17)
```

Figure 3A:
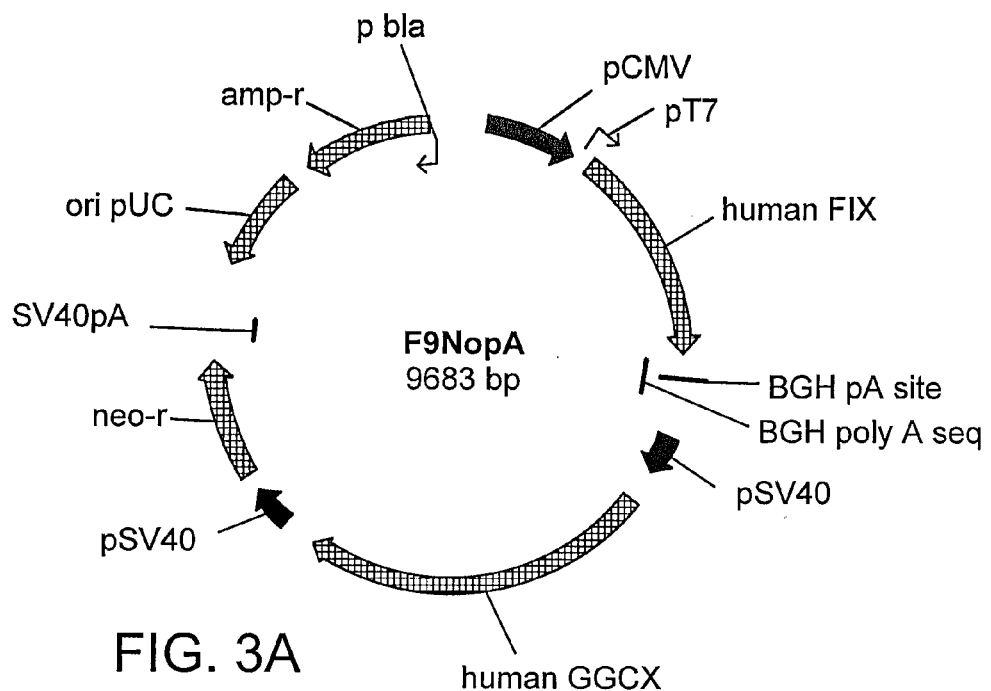
FIG. 3a represents a plasmid map of F9NopA (factor IX+GGCX) co-expression vector
Figure 3B:
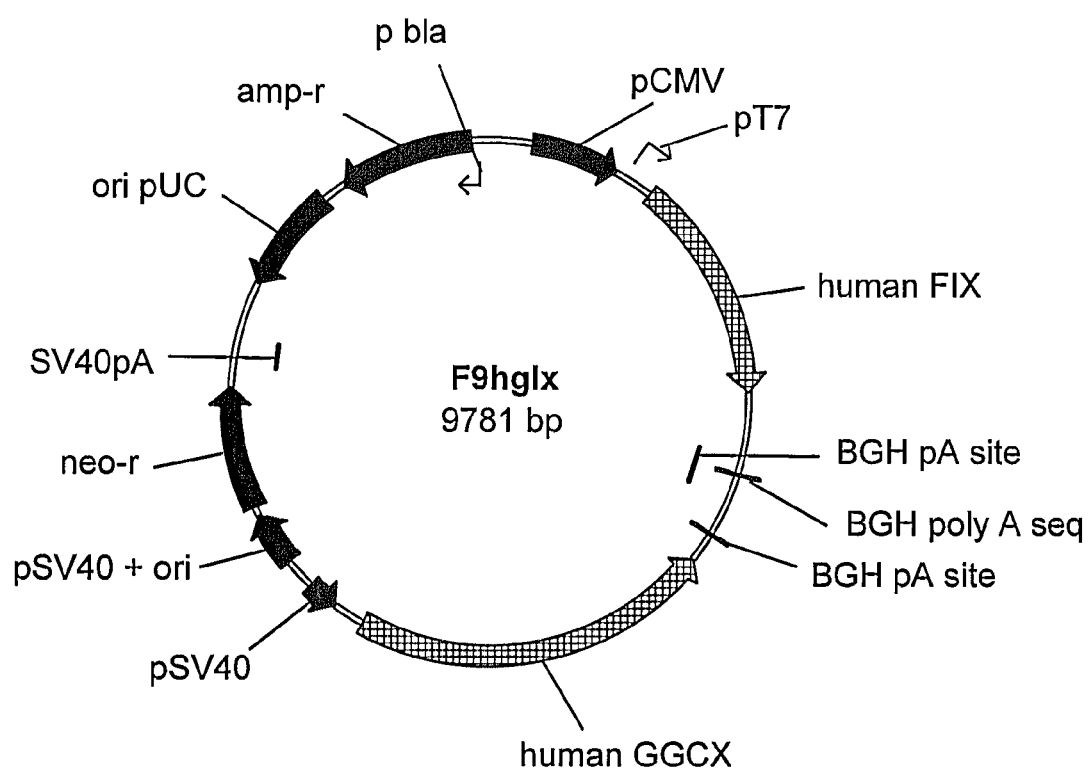
FIG. 3b represents a plasmid map of F9hglx (factor IX+GGCX) co-expression vector.

Cloning of the correct sequence was confirmed by DNA sequencing. The human FIX fragment was PCR amplified using Pfx polymerase (Invitrogen) and the cloning primers to produce a blunt ended fragment. The blunt-ended fragment was phosphorylated using T4 polynucleotide kinase, and cloned into the EcoRV digested and de-phosphorylated pCDNA-GGCX vectors from Ex. 1 and Ex 4. In this way constructs for co-expression of human FIX and GGCX analogous to the co-expression constructs used for production of human prothrombin (Ex. 1 and 4) were obtained. Cloning of the correct sequences was confirmed by DNA sequencing and transient expression in COS-7 cells. The vector construct F9NopA can be seen in FIG. 3a and the vector construct F9hglx is shown in FIG. 3b. The difference between the vectors F9NopA and F9hglx is the transcription direction of the GGCX gene. The F9NopA nucleotide sequence is shown in SEQ ID NO: 14 and the F9hglx nucleotide sequence is shown in SEQ ID NO: 15

Establishment of Cell Lines Producing rhFIX

The rhFIX constructs were transfected to CHO-S cells using the procedure described in Ex1. For each FIX construct approximately 3000 clones were screened for rhFIX expression by ELISA of cell supernates. Antibodies used were from Haemathology Technology Inc. and DakoCytomation. Clones were selected and adapted to growth in protein free chemically defined CHO medium. Cells were grown either in T-flasks at 37° C. or in spinner bottles at 32-37° C. $CO_2$ concentration was 5% for both types of cultures. The rhFIX produced was purified to homogeneity by Q-Sepharose anion exchange chromatography at pH 7.0. Recombinant hFIX activity was determined by Clotting assay using FIX deficient plasma (Precision Biologic). The best producing rhFIX clone obtained was N4D5, which was obtained using the F9NopA construct, produced up to 4 µg/ml active rhFIX grown in protein free chemically defined medium in T-flask. Grown in spinner bottle the same clone produced up to 7.1 µg/ml rhFIX. The overall productivity, also including incompletely carboxylated, non-active rhFIX, was estimated by Western blotting to be at least 30 µg/ml. The best producing clone obtained with the rhFIX construct F9hglx was P1G9 that produced 0.7 (T-flask)—1.3 (spinner) µg/ml rhFIX under similar conditions. The results indicate that rhFIX productivity improved by co-expression of GGCX at a low level using the F9NopA construct, but that co-expression of GGCX using construct F9hglx, was less beneficial. It was also noted that the F9NopA construct, giving rise to the N4D5 clone, generally gave higher ELISA signals than the F9hglx construct, giving rise to the P1G9 clone, in simultaneous screens for productivity during the cell line development procedure.

The productivity of the N4D5 cell line is approximately 4-6 better than previously published levels obtained under comparable conditions, wherein IC4, IG8, r-FIX BHK and r-FIX 293 is the name of the clones mentioned in the references (Table 5).

TABLE 5

Comparison of productivity from human FIX producing cell lines.

| Cell line/construct | Amount of active rhFIX produced | | Total productivity (μg/ml) | Reference |
|---|---|---|---|---|
| | T-flask (μg/ml) | Spinner (μg/ml) | | |
| N4D5/F9NopA CHO, low GGXC co-expr. | 4 | 7.1 | >30 | Example 6 |
| P1G9/F9hglx CHO, medium GGCX co-expr. | 0.7 | 1.3 | nd | Example 6 |
| IC4 CHO, HA (control) co-expr. | 0.9 | nd | 30 | Rehemtulla 1993. |
| IC4 CHO. High GGCX co-expr. | 1 | nd | 29 | Rehemtulla 1993. |
| IC4 | 0.9 | nd | 20 | U.S. Pat. No. 5,460,950 |
| 1G8 CHO | 1.5 | nd | 43 | Kaufman, RJ et al 1986 JBC 261: 9622-9628 |
| r-FIX BHK | 0.004/24 h | nd | 0.004/24 h | Hallgren 2002 |
| r-FIX 293 | 0.004/24 h | nd | 0.004/24 h | Hallgren 2002 |

EXAMPLE 7

Real-Time RT-PCR Analyses of the Expression of γ-Carboxylase and Factor IX in CHO-S Cell Lines by Measuring Amount of mRNA Recombinant hFIX-producing clones were grown in spinner bottles at 32-37° C., in 100 ml protein free chemically defined medium supplemented with Vitamin K. Samples of 5-10 ml were collected at peak rhFIX concentration and analysed for content of human FIX and GGCX transcripts, as well as transcripts of the GAPDH control (house-keeping) gene. Procedure was as in example 3. Primers for rhFIX were as follows:
Human Factor IX Primers

```
                                    (SEQ ID NO: 18)
5' AATAGTGCTGATAACAAGGTGGTTTG 3' Forward primer (SEQ ID NO: 19)
5' CACTGCTGGTTCACAGGACTTCT 3' Reverse primer (SEQ ID NO: 20)
5' TCCTGTACTGAGGGATATCGACTTGCAGAAAAC 3' Probe
```

Amplicon length 84 bp

Messenger RNA levels were found to peak at different days depending on culture temperature and culture inoculum size. Peak levels of mRNA were found to correspond well with peak concentration of rhFIX in the culture medium.

TABLE 6

Results from Real-Time RT-PCR analyses of rhFIX-producing clones.

| Cell line-batch | Day of culture | $2^{\wedge}$-delta Ct FIX | $2^{\wedge}$-delta Ct GGCX | mRNA ratio FIX:GGCX |
|---|---|---|---|---|
| N4D5-100 | 11 | 0.255253 | 0.005461 | 47:1 |
| N4D5-2 | 14 | 0.264866 | 0.006201 | 43:1 |
| P1G9-A | 6 | 0.022982 | 0.005601 | 4:1 |
| P1G9-B | 8 | 0.04181 | 0.007687 | 5:1 |

From Real-Time RT-PCR analyses we also found that, although $2^{\wedge}$-delta Ct-values varied with culture time and conditions, the FIX:GGCX mRNA ratios were approximately the same for each clone. For the best rhFIX-producing clone N4D5 the ratio was approximately 45:1. Analyses of another clone, P1G9, gave a lower ratio of approximately 4.5:1. The P1G9 clone produced only 20% of the amount rhFTX produced by N4D5.

The invention claimed is:

1. An isolated cell comprising:
a first nucleic acid comprising a first expression control sequence operably linked to a nucleotide sequence encoding a protein requiring gamma-carboxylation; and
a second recombinant nucleic acid comprising a second expression control sequence operably linked to a nucleotide sequence encoding a γ-glutamyl carboxylase, wherein the γ-glutamyl carboxylase is expressed from the second recombinant nucleic acid at a level between 1.5 and 5-fold above the level of γ-glutamyl carboxylase in the cell in the absence of the second recombinant nucleic acid.

2. The isolated cell of claim 1, wherein the protein requiring gamma-carboxylation is expressed and carboxylated in the cell.

3. The isolated cell of claim 1, wherein the first and second nucleic acids are located on separate expression vectors or the same expression vector.

4. The isolated cell of claim 1, wherein the first expression control sequence comprises a first promoter and the second expression control sequence comprises a second promoter, wherein the first promoter is stronger than the second promoter in the cell.

5. The isolated cell of claim 4, wherein the first promoter is selected from the group consisting of human cytomegalovirus (hCMV) immediate-early promoter, human elongation factor-1α subunit gene (pEF-1α) promoter, Rous sarcoma virus promoter (pRSV), and human ubiquitin promoter (pUbC), and the second promoter is selected from the group consisting of Simian Virus 40 (SV40) immediate early promoter, minimized human coagulation factor IX (FIX) promoter, and herpes simplex virus (HSV) thymidine kinase promoter.

6. The isolated cell of claim 4, wherein the second promoter is a modified version of the first promoter.

7. The isolated cell of claim 1, wherein the protein requiring carboxylation and the γ-glutamyl carboxylase expressed from the second recombinant nucleic acid are expressed in the cell at a ratio of at least 10:1.

8. The isolated cell of claim 7, wherein the protein requiring carboxylation and the γ-glutamyl carboxylase expressed from the second recombinant nucleic acid are expressed in the cell at a ratio of between 10:1 to 500:1.

9. The isolated cell of claim 1, wherein the protein requiring carboxylation and the γ-glutamyl carboxylase expressed from the second recombinant nucleic acid are expressed in the cell at a ratio of between 25:1 to 250:1.

10. The isolated cell of claim 1, wherein the first expression control sequence comprises:
a Kozak sequence whereas the second expression control sequence does not; or
a wild type Kozak sequence and the second expression control sequence comprises a modified version of the wild type Kozak sequence, wherein the activity of the modified Kozak sequence in the cell is reduced relative to the activity of the wild type Kozak sequence in the cell.

11. The isolated cell of claim 1, wherein the cell comprises more copies of the first nucleic acid than the second recombinant nucleic acid.

12. The isolated cell of claim 1, wherein the γ-glutamyl carboxylase expressed from the second recombinant nucleic acid is a human protein.

13. The isolated cell of claim 1, wherein the protein requiring gamma-carboxylation is a human protein.

14. The isolated cell of claim 1, wherein the protein requiring gamma-carboxylation is coagulation factor VII, coagulation factor IX, coagulation factor II (prothrombin), coagulation factor X, Protein C, Protein S, Protein Z, Bone Gla protein, Matrix Gla protein, Growth arrest-specific protein 6, or Acanthophiinae FXa-like protein.

15. The isolated cell of claim 1, wherein the cell is selected from the group consisting of a mammalian cell, a yeast cell, and an insect cell.

16. An isolated cell comprising:
a first nucleic acid comprising a first expression control sequence operably linked to a nucleotide sequence encoding a protein requiring gamma-carboxylation; and
a second recombinant nucleic acid comprising a second expression control sequence operably linked to a nucleotide sequence encoding a γ-glutamyl carboxylase, wherein the γ-glutamyl carboxylase is expressed in the cell at a level less than or equal to 10% of the amount of the protein requiring gamma-carboxylation.

17. An expression vector comprising:
a first nucleic acid comprising a first expression control sequence operably linked to a nucleotide sequence encoding a protein requiring gamma-carboxylation; and
a second nucleic acid comprising a second expression control sequence operably linked to a nucleotide sequence encoding a γ-glutamyl carboxylase, wherein the first expression control sequence has higher transcriptional activity than the second expression control sequence.

18. The expression vector of claim 17, wherein the first expression control sequence comprises a first promoter selected from the group consisting of human cytomegalovirus (hCMV) immediate-early promoter, human elongation factor-1α subunit gene (pEF-1α) promoter, Rous sarcoma virus promoter (pRSV), and human ubiquitin promoter (pUbC), and the second expression control sequence comprises a second promoter selected from the group consisting of SV40 immediate early promoter, minimized FIX promoter, and HSV thymidine kinase promoter.

19. The expression vector of claim 18, wherein the first promoter is hCMV immediate-early promoter, and the second promoter is SV40 immediate early promoter.

20. The expression vector of claim 17, wherein the first nucleic acid further comprises a bovine growth hormone (BGH) polyadenylation signal linked to the nucleotide sequence encoding a protein requiring gamma-carboxylation and proximal to the first expression control sequence.

21. The expression vector of claim 17, wherein the first expression control sequence comprises a first promoter and the second expression control sequence comprises second promoter, and wherein the second promoter is a modified version of the first promoter.

22. The expression vector of claim 17, wherein the first expression control sequence comprises:
a Kozak sequence whereas the second expression control sequence does not; or
a wild type Kozak sequence and the second expression control sequence comprises a modified version of the wild type Kozak sequence, wherein the activity of the modified Kozak sequence is reduced relative to the activity of the wild type Kozak sequence.

* * * * *